(12) United States Patent
Kasai et al.

(10) Patent No.: US 7,803,898 B2
(45) Date of Patent: *Sep. 28, 2010

(54) AMINOQUINOXALINE COMPOUND, POLYAMINOQUINOXALINE COMPOUND, AND USE THEREOF

(75) Inventors: Mikio Kasai, Funabashi (JP); Hitoshi Furusho, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 1048 days.

This patent is subject to a terminal disclaimer.

(21) Appl. No.: 10/585,757

(22) PCT Filed: Jan. 12, 2005

(86) PCT No.: PCT/JP2005/000209

§ 371 (c)(1),
(2), (4) Date: Jul. 12, 2006

(87) PCT Pub. No.: WO2005/068439

PCT Pub. Date: Jul. 28, 2005

(65) Prior Publication Data

US 2009/0030176 A1    Jan. 29, 2009

(30) Foreign Application Priority Data

Jan. 13, 2004    (JP) ............................. 2004-005892
Aug. 31, 2004    (JP) ............................. 2004-251766
Sep. 3, 2004     (JP) ............................. 2004-256620

(51) Int. Cl.
C08G 73/06    (2006.01)

(52) U.S. Cl. .................. 528/423; 528/424; 544/353; 257/40

(58) Field of Classification Search .................. 257/40; 528/423, 424
See application file for complete search history.

(56) References Cited

U.S. PATENT DOCUMENTS

| | | | |
|---|---|---|---|
| 4,356,429 A | 10/1982 | Tang | |
| 6,258,337 B1 | 7/2001 | Sonobe et al. | |
| 6,310,762 B1 | 10/2001 | Okamura et al. | |
| 6,548,670 B1 | 4/2003 | Burdeniuc | |
| 6,738,252 B2 | 5/2004 | Okamura et al. | |
| 2002/0073534 A1 | 6/2002 | Kurosaki et al. | |
| 2003/0215701 A1* | 11/2003 | Nagasaki et al. | 429/94 |
| 2006/0128937 A1 | 6/2006 | Nagasaki et al. | |
| 2009/0030176 A1 | 1/2009 | Kasai et al. | |

FOREIGN PATENT DOCUMENTS

| | | |
|---|---|---|
| EP | 1 361 244 A1 | 11/2003 |
| EP | 1 640 402 A1 | 3/2006 |
| JP | 7-70306 A | 3/1995 |
| JP | 11-506123 A | 6/1999 |
| JP | 11-214270 A | 8/1999 |
| JP | 11-297577 A | 10/1999 |
| JP | 11-317333 A | 11/1999 |
| JP | 2000-53956 A | 2/2000 |
| JP | 2000-68164 A | 3/2000 |
| JP | 2000-100668 A | 4/2000 |
| JP | 2000-509730 A | 8/2000 |
| JP | 2002-134162 A | 5/2002 |
| JP | 2003-55351 A | 2/2003 |
| JP | 2004-8356 A | 3/2004 |
| SU | 592823 | 2/1978 |
| WO | WO-97/32873 A1 | 9/1997 |
| WO | WO-98/38186 A1 | 9/1998 |
| WO | WO-2004/111108 A1 | 12/2004 |

OTHER PUBLICATIONS

Volf et al., Solid State Ionics, vol. 154-155, 2002, pp. 57-63.
Albini et al., Journal of the Chemical Society, Perkin Transactions 1, vol. 3, 1978, pp. 299-303.
Furusho et al., Journal of Photopolymer Science and Technology, vol. 15, No. 1, 2002, pp. 133-136.
Bauldreay et al., Electrochimica Acta, vol. 28, No. 11, 1983, pp. 1515-1522.
Pfeiffer et al., Journal of Organic Chemistry, vol. 31, No. 10, Oct. 1966, pp. 3384-3390.
Gaertner et al., Tetrahedron, vol. 18, 1962, pp. 1105-1114.
Cookson, Journal of the Chemical Society, 1953, pp. 1328-1331.
Platt et al., Journal of the Chemical Society, No. 429, 1948, pp. 2129-2134.

(Continued)

*Primary Examiner*—Randy Gulakowski
*Assistant Examiner*—Shane Fang
(74) *Attorney, Agent, or Firm*—Birch, Stewart, Kolasch & Birch, LLP

(57) ABSTRACT

An aminoquinoxaline compound represented by the following formula (1a), and a polyaminoquinoxaline compound obtained by polymerizing the aminoquinoxaline compound,

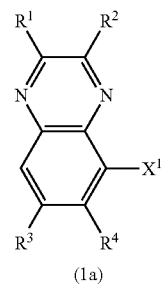

(1a)

wherein $R^1$ and $R^2$ independently represent a hydrogen atom, a hydroxyl group, a $C_1$-$C_{10}$ alkyl group, a $C_1$-$C_{10}$ alkoxy group, or the like, $R^3$ and $R^4$ independently represent a hydrogen atom, a halogen atom, a cyano group, a nitro group, an amino group, a $C_1$-$C_{10}$ alkyl group, a $C_1$-$C_{10}$ alkoxy group or the like, and $X^1$ represents —NH—$R^5$—$NH_2$ or —NH—$R^6$.

34 Claims, No Drawings

OTHER PUBLICATIONS

R. H. Partridge, Polymer, the United Kingdom, Jun. 1983, vol. 24, pp. 748-754.
Seiji Hayashi et al., Japanese Journal of Applied Physics, vol. 25, No. 9, Sep. 1986, pp. L773-L775.
C. W. Tang et al., Applied Physics Letters, United States of America, Sep. 21, 1987, vol. 51, (12) pp. 913-915.
Denki Kagaku, Electrochemistry and Industrial Physicochemistry, 1986, vol. 54, No. 4, pp. 306-311.
S. Tanaka et al., Synthetic Metals, vol. 69 (1995), pp. 599-600.
Journal of the American Chemical Society, the United States of America, 1995, vol. 117, No. 25, pp. 6791-6792.
Chen et al., Acta Pharmaceutica Sinica, vol. 27, No. 6, pp. 418-422, (1992).
Nowak et al., Database CAPLUS on STN, AN 1997:615604, DN 127: 293190, vol. 93, No. 6, pp. 22-28, (1996).
Thomas et al., Journal of Electroanalytical Chemistry, vol. 501, No. 1-2, pp. 235-240, (2001).
Rudge et al., Journal of Power Sources, vol. 47, 1994, pp. 89-107.
Mukai, Dai 44 Kai Battery Symposium in Japan, Nov. 4, 2003, pp. 672-673. English Abstract.
English translation of International Preliminary Report on Patentability (Form PCT/IB/338 and 373), 2006.
English translation of the Written Opinion of the International Searching Authority (Form PCT/ISA/237), 2006.
Aug. 20, 2009 Office Action which issued in U.S. Appl. No. 10/588,232.

* cited by examiner

AMINOQUINOXALINE COMPOUND, POLYAMINOQUINOXALINE COMPOUND, AND USE THEREOF

PARTIES TO A JOINT RESEARCH AGREEMENT

The claimed invention was made by or on behalf of YAMAGUCHI UNIVERSITY and/or NISSAN CHEMICAL INDUSTRIES, LTD., who are each parties to a joint research agreement that was in effect on or before the date the claimed invention was made. The claimed invention was made as the result of activities undertaken within the scope of the joint research agreement.

TECHNICAL FIELD

This invention relates to an aminoquinoxaline compound and a polyaminoquinoxaline compound that is a polymer of the aminoquinoxaline compound, and also to the use thereof.

BACKGROUND ART

Aromatic compounds having a two-dimensionally spreading π-conjugating system, and heterocyclic compounds having a hetero atom have been recently utilized in various types of electronic devices while taking advantage of emission characteristics and electron and hole transport characteristics thereof. For instance, organic electroluminescent devices are broadly classified into a polymer-based device using a π-conjugating system and a low molecular weight material-based device where individual layers imparted with functional properties are built up. Especially, with low molecular weight materials, carrier mobility and fluorescence emission characteristic are required, which has, in turn, required optional changes in bandgap in the course of development of derivatives. Because of the importance of film properties, these materials have been essentially required to form a stable amorphous film (see, for example, Non-Patent Document 1; Non-Patent Document 2; Non-Patent Document 3; and Patent Document 1).

In cells, the control in the oxidation and reduction potential of compound is required (see, for example, Non-Patent Document 4). The electrode active materials used for cells should have such a relation with an electrolytic solution that an oxidation-reduction potential is within a decomposition voltage of an electrolytic solution, and thus, the control of the oxidation-reduction potential is an important problem to solve.

With respect to semiconducting characteristics, studies have been generally made on π-conjugating polymers so as to achieve narrow bandgapping. Usually, π-conjugating polymers are insoluble in solvent and are difficult to handle, with a difficulty in structural control. For another measure of narrowing a bandgap, there is known a method of two-dimensionally spreading a π-conjugating system (see, for example, Non-Patent Document 5 and Non-Patent Document 6). These materials used for this method are also insoluble and infusible and are thus difficult to handle. Ordinary conjugating polymers behave as an impurity semiconductor by doping, with a difficulty in stably preparing p-type and n-type semiconductors from one material.

Non-Patent Document 1: Polymer, the United Kingdom, 1983, Vol. 24, P. 748
Non-Patent Document 2: Japanese Journal of Applied Physics, 1986, Vol. 25, P. 773
Non-Patent Document 3: Applied Physics Letters, United States of America, 1987, Vol. 51, p. 913
Non-Patent Document 4: Electrochemistry and Industrial Physicochemistry, 1986, Vol. 54, p. 306
Non-Patent Document 5: Synthetic Meals, the United States of America, 1995, Vol. 69, p. 599-600
Non-Patent Document 6: Journal of the American Chemical Society, the United States of America, 1995, Vol. 177, No. 25, p. 6791-6792
Patent Document 1: U.S. Pat. No. 4,356,429

DISCLOSURE OF THE INVENTION

Problems to be Solved by the Invention

Under these circumstances, the invention has been accomplished as a result of intensive studies on compounds having novel molecular structures.

An object of the invention is to provide an aminoquinoxaline compound and a polyaminoquinoxaline compound which is excellent in heat resistance, soluble in water or organic solvents, and controllable in polarization factor and electrochemical oxidation-reduction potential and which shows a distinct color change through chemical or electrochemical oxidation and reduction and exhibits electric conductivity and carrier mobility on their own.

Another object of the invention is to use novel aminoquinoxaline compounds and polyaminoquinoxaline compounds after forming these compounds into products such as a film obtained by spin coating and the like, materials for organic electroluminescent devices, semiconductors, semiconductor devices, materials for nonlinear optics and the like.

Means for Solving the Problems

The invention relates to those compounds and the use thereof recited in [1] to [34] below.

[1] An aminoquinoxaline compound of the following formula (1a)

[Chemical Formula 1]

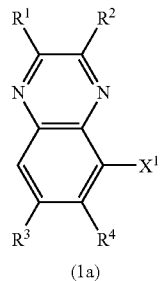

(1a)

wherein $R^1$ and $R^2$ independently represent a hydrogen atom, a hydroxyl group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^1$ and $R^2$ are, respectively, the above-defined phenyl, pyridyl, biphenyl, naphthyl, thienyl, pyrolyl, furyl or condensed heteroaryl group, these groups may be joined through a single bond;

$R^3$ and $R^4$ independently represent a hydrogen atom, a halogen atom, a cyano group, a nitro group, an amino group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^3$ and $R^4$ are, respectively, the above-defined phenyl, pyridyl, biphenyl, naphthyl, thienyl, pyrolyl, furyl or condensed heteroaryl group, these groups may be joined through a single bond;

$X^1$ represents —NH—$R^5$—$NH_2$ or —NH—$R^6$;

$R^5$ represents a $C_1$-$C_{10}$ alkylene group, a —C(O)$CH_2$—, —$CH_2$C(O)—, a divalent benzene ring which may be substituted with Y, a divalent pyridine ring which may be substituted with Y, a divalent biphenyl group which may be substituted with Y, a divalent naphthalene ring which may be substituted with Y, a divalent thiophene ring which may be substituted with Y, a pyrrole ring which may be substituted with Y a furan ring which may be substituted with Y, or a condensed hetero ring which may be substituted with Y;

$R^6$ represents a hydrogen atom, a $C_1$-$C_{10}$ alkyl group, an acetyl group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y, or a condensed heteroaryl group which may be substituted with Y;

Y represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z provided that if Y is two or more in number, Y may be the same or different; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group provided that if Z is two or more in number, Z may be the same or different.

[2] The aminoquinoxaline compound recited in [1] above, wherein $R^1$ and $R^2$ in the above formula (1) independently represent a group of the following formula (2)

[Chemical Formula 2]

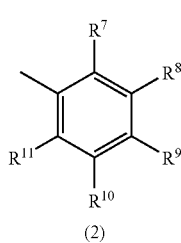

(2)

wherein $R^7$-$R^{11}$ independently represent a hydrogen atom, a halogen atom, a cyano group, a nitro group, an amino group, an epoxy group, a vinyl group, a $C_1$-$C_{10}$ alkyl group, a $C_1$-$C_4$ haloalkyl group, a $C_1$-$C_{10}$ alkoxy group, a $C_1$-$C_4$ cyanoalkyl group, a phenyl group which may be substituted with Z, a naphthyl group which may be substituted with Z or a thienyl group which may be substituted with Z; and Z has the same meanings as defined in the above formula (1a).

[3] The aminoquinoxaline compound recited in [1] above, wherein $R^1$ and $R^2$ in the above formula (1) independently represent a group of the following formula (3)

[Chemical Formula 3]

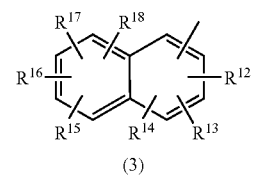

(3)

wherein $R^{12}$-$R^{18}$ independently represent, each substituted at an arbitrary position on the ring of the formula, a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z has the same meanings as defined in the above formula (1a).

[4] The aminoquinoxaline compound recited in [1] above, wherein $R^1$ and $R^2$ in the above formula (1) independently represent a group of the following formula (4)

[Chemical Formula 4]

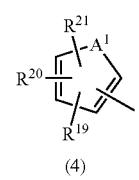

(4)

wherein $R^{19}$-$R^{21}$ independently represent, each substituted at an arbitrary position on the ring of the formula, a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z;

Z has the same meanings as defined in the above formula (1a); and $A^1$ represents NH, O or S.

[5] The aminoquinoxaline compound recited in [1] above, wherein $R^1$ and $R^2$ in the above formula (1) independently represent a group of the following formula (5)

[Chemical Formula 5]

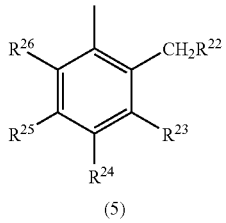

(5)

wherein $R^{22}$ represents a halogen atom or a cyano group, $R^{23}$-$R^{26}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z has the same meanings as defined in the above formula (1a).

[6] The aminoquinoxaline compound recited in any one of [1] to [5] above, wherein $R^5$ in the formula (1) represents a group of the following formula (6)

[Chemical Formula 6]

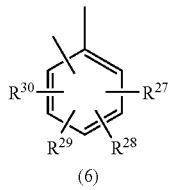

(6)

wherein $R^{27}$-$R^{30}$ independently represent, each substituted at an arbitrary position on the ring of the formula, a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z has the same meanings as defined in the above formula (1a).

[7] The aminoquinoxaline compound recited in any one of [1] to [5] above, wherein $R^5$ in the formula (1) represents a group of the following formula (7)

[Chemical Formula 7]

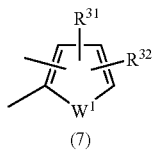

(7)

wherein $R^{31}$-$R^{32}$ independently represent, each substituted at an arbitrary position on the ring of the formula, a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z;

Z has the same meanings as defined in the above formula (1a); and $W^1$ represents NH, O or S.

[8] The aminoquinoxaline compound recited in any one of [1] to [5] above, wherein $R^5$ in the formula (1) represents a group of the following formula (8)

[Chemical Formula 8]

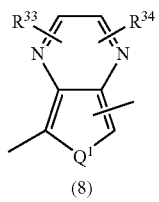

(8)

wherein $R^{33}$-$R^{34}$ independently represent, each substituted at an arbitrary position on the ring of the formula, a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z;

Z has the same meanings as defined in the above formula (1a); and $Q^1$ represents NH, O or S.

[9] The aminoquinoxaline compound recited in any one of [1] to [5] above, wherein $R^5$ in the formula (1) represents a group of the following formula (9)

[Chemical Formula 9]

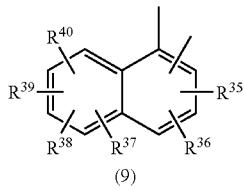

(9)

wherein $R^{35}$-$R^{40}$ independently represent, each substituted at an arbitrary position on the ring of the formula, a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z has the same meanings as defined in the above formula (1a).

[10] The aminoquinoxaline compound recited in any one of [1] to [5] above, wherein $R^6$ in the formula (1) represents a group of the following formula (10)

[Chemical Formula 10]

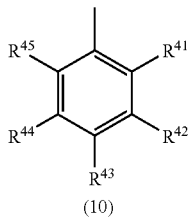

(10)

wherein $R^{41}$-$R^{45}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z has the same meanings as defined in the above formula (1a).

[11] The aminoquinoxaline compound recited in any one of [1] to [5] above, wherein $R^6$ in the formula (1) represents a group of the following formula (11)

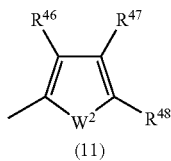

(11)

[Chemical Formula 11]

wherein $R^{46}$-$R^{48}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z;

Z has the same meanings as defined in the above formula (1a); and $W^2$ represents NH, O or S.

[12] The aminoquinoxaline compound recited in any one of [1] to [5] above, wherein $R^6$ in the formula (1) represents a group of the following formula (12)

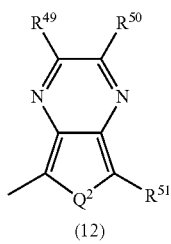

(12)

[Chemical Formula 12]

wherein $R^{49}$-$R^{51}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z;

Z has the same meanings as defined in the above formula (1a); and $Q^2$ represents NH, O or S.

[13] The aminoquinoxaline compound recited in any one of [1] to [5] above, wherein $R^6$ in the formula (1) represents a group of the following formula (13)

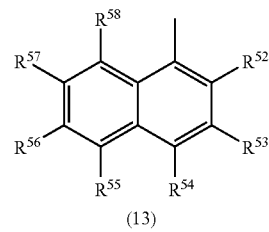

(13)

[Chemical Formula 13]

wherein $R^{52}$-$R^{58}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z has the same meanings as defined in the above formula (1a).

[14] The aminoquinoxaline compound recited in [1] above, wherein the group formed by bonding $R^1$ and $R^2$ through a singe bond in the formula (1) is represented by the formula (14)

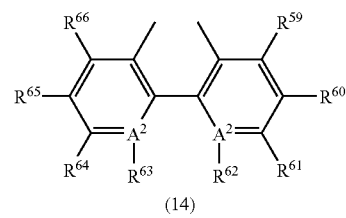

(14)

[Chemical Formula 14]

wherein $A^2$ are each CN or N, $R^{59}$-$R^{66}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z has the same meanings as defined in the above formula (1a), provided that when $A^2$ represents N, $R^{62}$ and $R^{63}$ are both non-existent.

[15] An aminoquinoxaline compound of the following formula (1b),

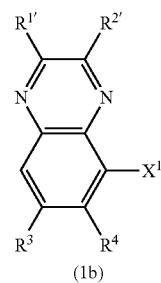

(1b)

[Chemical Formula 15]

wherein $R^{1'}$ and $R^{2'}$ join together to form —$CH_2CH_2CH_2$—, —$CH_2CH_2O$—, —$OCH_2CH_2$—, —$CH_2OCH_2$—, —OCH$_2$O—, —CH$_2$CH$_2$S—, —SCH$_2$CH$_2$—, —CH$_2$SCH$_2$—, —CH$_2$CH$_2$N(R')—, —N(R')CH$_2$CH$_2$—, —CH$_2$N(R')CH$_2$—, —CH$_2$CH$_2$CH$_2$CH$_2$—, —CH$_2$CH$_2$CH$_2$O—, —OCH$_2$CH$_2$CH$_2$—, —CH$_2$CH$_2$OCH$_2$—, —CH$_2$OCH$_2$CH$_2$—, —CH$_2$OCH$_2$O—, —OCH$_2$CH$_2$O—, —SCH$_2$CH$_2$S—, —OCH$_2$CH$_2$S—, —SCH$_2$CH$_2$O—, —CH$_2$CH═CH—, —CH═CHCH$_2$—, —OCH═CH—, —CH═CHO—, —SCH═CH—, —CH═CHS—, —N(R')CH═CH—, —CH═CHN(R')—, —OCH═N—, —N═CHO—, —SCH═N—, —N═CHS—, —N(R')CH═N—, —N═CHN(R')—, —N(R')N═CH—, —CH═N(R')N—, —CH═CHCH═CH—, —OCH$_2$CH═CH—, —CH═CHCH$_2$O—, —N═CHCH═CH—, —CH═CHCH═N—, —N═CHCH═N—, —N═CHN═CH—, or —CH═NCH═N— wherein a hydrogen atom bonded to a carbon atom of these groups may be substituted with Y, and R' represents a hydrogen atom, a $C_1$-$C_{10}$ alkyl group, a $C_1$-$C_{10}$ haloalkyl group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z, or a condensed heteroaryl group which may be substituted with Z;

$R^3$, $R^4$, $X^1$, Y and Z have the same meanings as defined in the above formula (1a).

[16] The aminoquinoxaline compound of the following formula (1c),

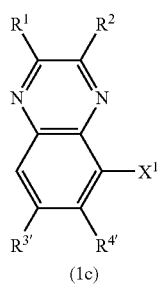

(1c)

[Chemical Formula 16]

wherein $R^{3'}$ and $R^{4'}$ join together to form —CH$_2$CH$_2$CH$_2$—, —CH$_2$CH$_2$O—, —OCH$_2$CH$_2$—, —CH$_2$OCH$_2$—, —OCH$_2$O—, —CH$_2$CH$_2$S—, —SCH$_2$CH$_2$—, —CH$_2$SCH$_2$—, —CH$_2$CH$_2$N(R')—, —N(R')CH$_2$CH$_2$—, —CH$_2$N(R')CH$_2$—, —CH$_2$CH$_2$CH$_2$CH$_2$—, —CH$_2$CH$_2$CH$_2$O—, —OCH$_2$CH$_2$CH$_2$—, —CH$_2$CH$_2$OCH$_2$—, —CH$_2$OCH$_2$CH$_2$—, —CH$_2$OCH$_2$O—, —OCH$_2$CH$_2$O—, —SCH$_2$CH$_2$S—, —OCH$_2$CH$_2$S—, —SCH$_2$CH$_2$O—, —CH$_2$CH═CH—, —CH═CHCH$_2$—, —OCH═CH—, —CH═CHO—, —SCH═CH—, —CH═CHS—, —N(R')CH═CH—, —CH═CHN(R')—, —OCH═N—, —N═CHO—, —SCH═N—, —N═CHS—, —N(R')CH═N—, —N═CHN(R')—, —N(R')N═CH—, —CH═N(R')N—, —CH═CHCH═CH—, —OCH$_2$CH═CH—, —CH═CHCH$_2$O—, —N═CHCH═CH—, —CH═CHCH═N—, —N═CHCH═N—, —N═CHN═CH—, or —CH═NCH═N— wherein a hydrogen atom bonded to a carbon atom of these groups may be substituted with Y, and R' represents a hydrogen atom, a $C_1$-$C_{10}$ alkyl group, a $C_1$-$C_{10}$ haloalkyl group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z, or a condensed heteroaryl group which may be substituted with Z;

$R^1$, $R^2$, $X^1$, Y and Z have the same meanings as defined in the above formula (1a).

[17] An aminoquinoxaline compound of the following formula (1d),

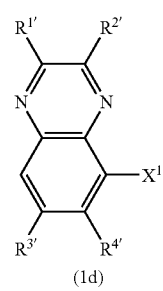

(1d)

[Chemical Formula 17]

wherein $R^{1'}$, $R^{2'}$, $R^{3'}$, $R^{4'}$ and $X^1$ have the same meanings as defined in the above formulae (1a), (1b) and (1c).

[18] The aminoquinoxaline compound as recited in [15] or [17] above, wherein the group formed by joining $R^{1'}$ and $R^{2'}$ together is of the formula (15)

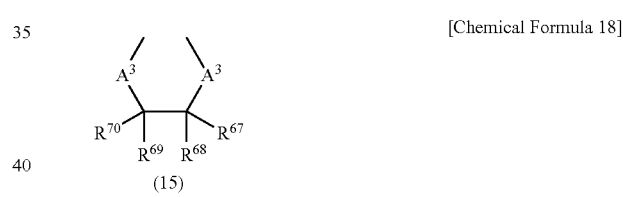

(15)

[Chemical Formula 18]

wherein $A^3$ represents O or S, and $R^{67}$-$R^{70}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z has the same meanings as defined in the above formula (1a).

[19] The aminoquinoxaline compound as recited in [16] or [17] above, wherein the group formed by joining $R^{3'}$ and $R^{4'}$ together is of the formula (16)

(16)

[Chemical Formula 19]

wherein $A^4$ represents O or S, and $R^{71}$-$R^{74}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z has the same meanings as defined in the above formula (1a).

[20] The aminoquinoxaline compound as recited in [17] above, wherein the group formed by joining $R^{3'}$ and $R^{4'}$ together is of the formula (17)

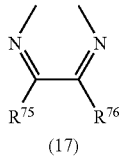

[Chemical Formula 20]

(17)

wherein $R^{75}$ and $R^{76}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z has the same meanings as defined in the above formula (1a).

[21] A polyaminoquinoxaline compound having recurring units of the following formula (18a) obtained by polymerizing the monomer recited in [1] above,

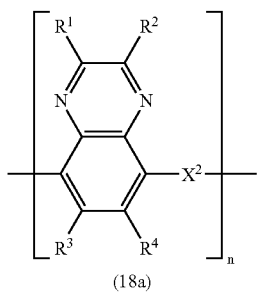

[Chemical Formula 21]

(18a)

wherein $R^1$, $R^2$, $R^3$ and $R^4$ have the same meanings as defined in the formula (1a);

$X^2$ represents —NH—$R^{77}$—NH— or —NH—$R^{78}$—;

$R^{77}$ and $R^{78}$ independently represent a $C_1$-$C_{10}$ alkylene group, a —C(O)CH$_2$—, —CH$_2$C(O)—, a divalent benzene ring which may be substituted with Y, a divalent pyridine ring which may be substituted with Y, a divalent biphenyl group which may be substituted with Y, a divalent naphthalene ring which may be substituted with Y, a divalent thiophene ring which may be substituted with Y, a divalent pyrrole ring which may be substituted with Y, a divalent furan ring which may be substituted with Y, or a condensed hetero ring which may be substituted with Y;

Y has the same meanings as defined in the above formula (1a); and n is an integer of 2 or over.

[22] A polyaminoquinoxaline compound having recurring units of the following formula (18b) obtained by polymerizing the monomer recited in [15] above,

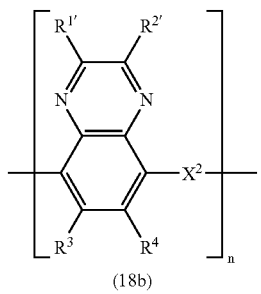

[Chemical Formula 22]

(18b)

wherein $R^{1'}$, $R^{2'}$, $R^3$, $R^4$, $X^2$ and n have the same meanings as defined in the above formulae (1a), (1b) and (18a).

[23] A polyaminoquinoxaline compound having recurring units of the following formula (18c) obtained by polymerizing the monomer recited in [16] above,

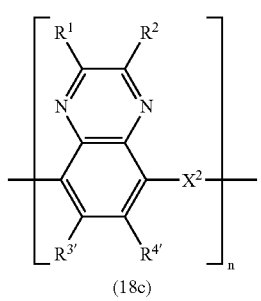

[Chemical Formula 23]

(18c)

wherein $R^1$, $R^2$, $R^{3'}$, $R^{4'}$, $X^2$ and n have the same meanings as defined in the above formulae (1a), (1c) and (18a).

[24] A polyaminoquinoxaline compound having recurring units of the following formula (18d) obtained by polymerizing the monomer recited in [17] above,

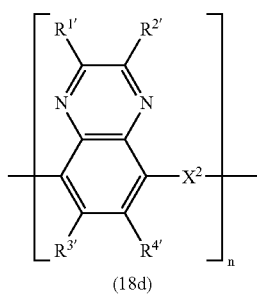

[Chemical Formula 24]

(18d)

wherein $R^{1'}$, $R^{2'}$, $R^{3'}$, $R^{4'}$, $X^2$ and n have the same meanings as defined in the above formulae (1b), (1c) and (18a).

[25] A film obtained by use of an aminoquinoxaline compound or a polyaminoquinoxaline compound as recited in any one of [1] to [24] above.

[26] The film as recited in [25] above wherein the film is prepared by spin coating, casting or vacuum deposition.

[27] The film as recited in [25] above, wherein the film is obtained by compression molding.

[28] An electro chromic device made by use of an aminoquinoxaline compound or a polyaminoquinoxaline compound as recited in any one of [1] to [24] above.
[29] A semiconductor device made by use of an aminoquinoxaline compound or a polyaminoquinoxaline compound as recited in any one of [1] to [24] above.
[30] A p-type semiconductor obtained by oxidizing, with an oxidizing agent or through electrochemical doping, an aminoquinoxaline compound or a polyaminoquinoxaline compound as recited in any one of [1] to [24] above.
[31] An n-type semiconductor obtained by reducing, with a reducing agent or through electrochemical doping, an aminoquinoxaline compound or a polyaminoquinoxaline compound as recited in any one of [1] to [24] above.
[32] A solar cell made by use of the p-type semiconductor recited in [30] above and the n-type semiconductor recited in [3] above.
[33] An organic electroluminescent device made by use of an aminoquinoxaline compound or a polyaminoquinoxaline compound as recited in any one of [1] to [24] above.
[34] A non-linear organic material made by use of an aminoquinoxaline compound or a polyaminoquinoxaline compound as recited in any one of [1] to [24] above.

Advantageous Effects of the Invention

The aminoquinoxaline compound or polyaminoquinoxaline compound of the invention has a good heat resistance and is readily controllable with respect to its electrochemical redox potential, and is very narrow in its own bandgap and has a intense fluorescent characteristic. Moreover, these compounds have an electron donatives group and an electron acceptive group in one molecule, thus exhibiting p-type and n-type semiconductive characteristics.

These compounds may be readily converted to films according to spin coating, dipping, casting or screen printing, and are applicable to as an active substance or electrode material of cell, a material for electroluminescent element, a semiconductor, a semiconductor device, a non-linear optic and the like. A high molecular weight film can be readily obtained from the aminoquinoxaline compound according to an electrolytic polymerization procedure, and the use of the film enables one to readily apply it as an active substance or electrode material of cell, a material for electroluminescent element, a semiconductor, a semiconductor device, a non-linear optic and the like.

BEST MODE FOR CARRYING OUT THE INVENTION

The invention is described in more detail below.
The compounds of the invention include the aminoquinoxaline compound of the afore-indicated formulae (1a) to (1d) and the polyaminoquinoxaline compounds of the afore-indicated formulae (18a) to (18d).

In the formulae (1a) to (1d) and (18a) to (18d), $R^1$ and $R^2$ independently represent a hydrogen atom, a hydroxyl group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^1$ and $R^2$ are, respectively, the above-defined phenyl, pyridyl, biphenyl, naphthyl, thienyl, pyrolyl, furyl or condensed heteroaryl group, these groups may be joined through a single bond;

$R^{1'}$ and $R^{2'}$ may join together to form —$CH_2CH_2CH_2$—, —$CH_2CH_2O$—, —$OCH_2CH_2$—, —$CH_2OCH_2$—, —$OCH_2O$—, —$CH_2CH_2S$—, —$SCH_2CH_2$—, —$CH_2SCH_2$—, —$CH_2CH_2N(R')$—, —$N(R')CH_2CH_2$—, —$CH_2N(R')CH_2$—, —$CH_2CH_2CH_2CH_2$—, —$CH_2CH_2CH_2O$—, —$OCH_2CH_2CH_2$—, —$CH_2CH_2OCH_2$—, —$CH_2OCH_2CH_2$—, —$CH_2OCH_2O$—, —$OCH_2CH_2O$—, —$SCH_2CH_2S$—, —$OCH_2CH_2S$—, —$SCH_2CH_2O$—, —$CH_2CH$=$CH$—, —$CH$=$CHCH_2$—, —$OCH$=$CH$—, —$CH$=$CHO$—, —$SCH$=$CH$—, —$CH$=$CHS$—, —$N(R')CH$=$CH$—, —$CH$=$CHN(R')$—, —$OCH$=$N$—, —$N$=$CHO$—, —$SCH$=$N$—, —$N$=$CHS$—, —$N(R')CH$=$N$—, —$N$=$CHN(R')$—, —$N(R')N$=$CH$—, —$CH$=$N(R')N$—, —$CH$=$CHCH$=$CH$—, —$OCH_2CH$=$CH$—, —$CH$=$CHCH_2O$—, —$N$=$CHCH$=$CH$—, —$CH$=$CHCH$=$N$—, —$N$=$CHCH$=$N$—, —$N$=$CHN$=$CH$—, or —$CH$=$NCH$=$N$— wherein a hydrogen atom bonded to a carbon atom of these groups may be substituted with Y, and R' represents a hydrogen atom, a $C_1$-$C_{10}$ alkyl group, a $C_1$-$C_{10}$ haloalkyl group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z, or a condensed heteroaryl group which may be substituted with Z.

More particularly, mention is made of those compounds of the following formulae (2) to (5), (14) and (15):

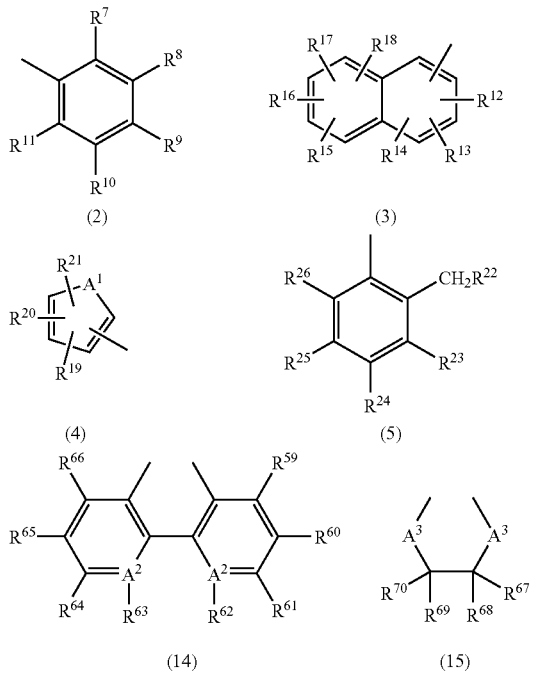

[Chemical Formula 25]

When the solubility of the aminoquinoxaline compound is taken into account, $R^1$, $R^2$, $R^{1'}$ and $R^{2'}$ should preferably be substituted with substituent Y. The substituent Y should preferably be a $C_1$-$C_{10}$ alkyl group or a $C_1$-$C_{10}$ alkoxy group, more preferably a $C_1$-$C_{10}$ alkyl group or a $C_1$-$C_5$ alkoxy group. Taking into account amorphousness such as in spin coating, t-butyl or t-butoxy is most preferred. With the alkyl group, the group may be brominates with NBS, and the brominates compound may be cyanided by reaction with NaCN.

On the other hand, $R^3$ and $R^4$ independently represent a hydrogen atom, a halogen atom, a cyano group, a nitro group, an amino group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^3$ and $R^4$ are, respectively, the above-defined phenyl, pyridyl, biphenyl, naphthyl, thienyl, pyrolyl, furyl or condensed heteroaryl group, these groups may be joined through a single bond;

$R^{3'}$ and $R^{4'}$ may join together to form —$CH_2CH_2CH_2$—, —$CH_2CH_2O$—, —$OCH_2CH_2$—, —$CH_2OCH_2$—, —$OCH_2O$—, —$CH_2CH_2S$—, —$SCH_2CH_2$—, —$CH_2SCH_2$—, —$CH_2CH_2N(R')$—, —$N(R')CH_2CH_2$—, —$CH_2N(R')CH_2$—, —$CH_2CH_2CH_2CH_2$—, —$CH_2CH_2CH_2O$—, —$OCH_2CH_2CH_2$—, —$CH_2CH_2OCH_2$—, —$CH_2OCH_2CH_2$—, —$CH_2OCH_2O$—, —$OCH_2CH_2O$—, —$SCH_2CH_2S$—, —$OCH_2CH_2S$—, —$SCH_2CH_2O$—, —$CH_2CH=CH$—, —$CH=CHCH_2$—, —$OCH=CH$—, —$CH=CHO$—, —$SCH=CH$—, —$CH=CHS$—, —$N(R')CH=CH$—, —$CH=CHN(R')$—, —$OCH=N$—, —$N=CHO$—, —$SCH=N$—, —$N=CHS$—, —$N(R')CH=N$—, —$N=CHN(R')$—, —$N(R')N=CH$—, —$CH=N(R')N$—, —$CH=CHCH=CH$—, —$OCH_2CH=CH$—, —$CH=CHCH_2O$—, —$N=CHCH=CH$—, —$CH=CHCH=N$—, —$N=CHCH=N$—, —$N=CHN=CH$—, or —$CH=NCH=N$— wherein a hydrogen atom bonded to a carbon atom of these groups may be substituted with Y, and R' has the same meaning as defined above.

From the standpoint of conductivity, when $R^3$ ($R^{3'}$) and $R^4$ ($R^{4'}$) are, respectively, an alkyl (alkylene) group or an alkoxyl (alkylenoxy) group, the groups should preferably have 1 to 5 carbon atoms. From the standpoint of providing good redox potential, $R^3$ and $R^4$ should preferably be a phenyl group, a naphthyl group or a thienyl group. In view of electric characteristics, these groups should preferably be substituted with substituent Y. Such a substituent Y preferably includes a $C_1$-$C_{10}$ alkyl group or a $C_1$-$C_{10}$ alkoxy group, more preferably a $C_1$-$C_5$ alkyl group or a $C_1$-$C_5$ alkoxy group.

Examples of $R^3$, $R^4$, $R^{3'}$ and $R^{4'}$ include, aside from those groups of the formulae (2) to (5) and (14) exemplified with respect to the $R^1$, $R^2$, $R^{1'}$ and $R^{2'}$, the groups of the following formulae (16) and (17).

[Chemical Formula 26]

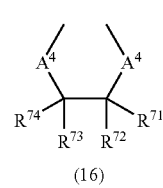 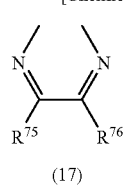

(16)  (17)

In the formulae (1a) to (1d), $R^5$ represents a $C_1$-$C_{10}$ alkylene group, —$C(O)CH_2$—, —$CH_2C(O)$—, a divalent benzene ring which may be substituted with Y, a divalent pyridine ring which may be substituted with Y, a divalent biphenyl group which may be substituted with Y, a divalent naphthalene ring which may be substituted with Y, a divalent thiophene ring which may be substituted with Y, a divalent pyrrole ring which may be substituted with Y, a divalent furan ring which may be substituted with Y, or a condensed hetero ring which may be substituted with Y. Specific examples are those groups of the following formulae (6) to (9):

[Chemical Formula 27]

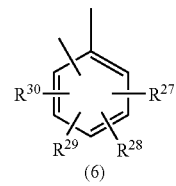 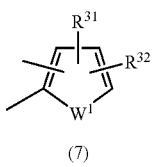

(6)  (7)

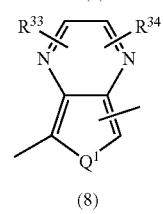 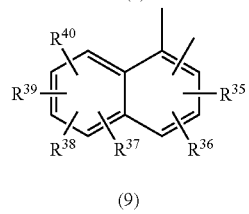

(8)  (9)

In the afore-indicated formulae (1a) to (1d), $R^6$ represents a hydrogen atom, a $C_1$-$C_{10}$ alkyl group, an acetyl group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y. Specific examples include those groups represented by the following formulae (10) to (13):

[Chemical Formula 28]

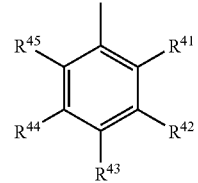 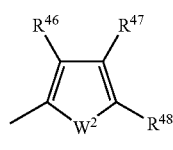

(10)  (11)

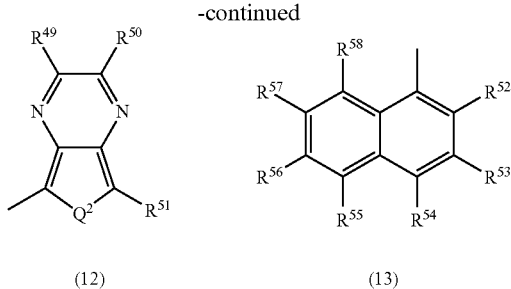

(12) (13)

In the afore-indicated formulae (18a) to (18d), $R^{77}$ and $R^{78}$ independently represent a $C_1$-$C_{10}$ alkylene group, —C(O)CH$_2$—, —CH$_2$C(O)—, a divalent benzene ring which may be substituted with Y, a divalent pyridine ring which may be substituted with Y, a divalent biphenyl group which may be substituted with Y, a divalent naphthalene ring which may be substituted with Y, a divalent thiophene ring which may be substituted with Y, a divalent pyrrole ring which may be substituted with Y, a divalent furan ring which may be substituted with Y, or a condensed hetero ring which may be substituted with Y.

From the standpoint of providing good redox potential, $R^5$, $R^{77}$ and $R^{78}$ should preferably be a divalent benzene ring, a divalent naphthalene ring or a divalent thiophene ring, respectively. In view of keeping stable electric characteristics such as of a film of a polyaminoquinoxaline compound, these cyclic substituents should preferably be substituted with substituent Y.

As to $R^6$, a phenyl group, a naphthyl group or a thienyl group is preferably used from the standpoint of providing good redox potential.

It will be noted that in order to keep stable amorphousness such as of a film of a polyaminoquinoxaline compound, it is preferred that $R^5$, $R^6$, $R^{77}$ and $R^{78}$ are, respectively, substituted with substituent Y. In this case, the substituent Y should preferably include a $C_1$-$C_{10}$ alkyl group or a $C_1$-$C_{10}$ alkoxy group, more preferably a $C_1$-$C_5$ alkyl group or a $C_1$-$C_5$ alkoxy group.

Although the molecular weight of the polyaminoquinoxaline compound represented by the formulae (18a) to (18d) is not critical, the weight average molecular weight preferably ranges 1,000 to 100,000, more preferably 4,000 to 50,000. In view of this, although n in the formulae (18a) to (18d) is a positive integer of 2 or more, n is preferably an integer sufficient to ensure the above-defined range of the weight average molecular weight, e.g. n=2 to 400.

In the above-indicated, respective formulae, the $C_1$-$C_{10}$ alkyl group may be linear, branched or cyclic and includes, for example, methyl, ethyl, n-propyl, i-propyl, n-butyl, i-butyl, t-butyl, s-butyl, n-pentyl, n-hexyl, 2-ethylpropyl, 2,2-dimethylpropyl, 1,2-dimethylpropyl, 1,1,2-trimethylpropyl, 1,2,2-trimethylpropyl, 1-ethyl-1-methylropyl, 1-ethyl-2-methylpropyl, 1-methylbutyl, 2-methylbutyl, 3-methylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-methylpentyl, 2-methylpentyl, 2-methylpentyl, 3-methylpentyl, 4-methylpentyl and the like. It will be noted that for the $C_1$-$C_{10}$ alkylene groups, mention is made of those groups wherein one hydrogen atom is eliminated from the above-indicated alkyl groups.

For the $C_1$-$C_{10}$ haloalkyl groups, those groups wherein at least one hydrogen atom of the above-indicated alkyl groups is substituted with a halogen atom are mentioned. It should be noted that the halogen atom may be any of chlorine, bromine, iodine and fluorine atoms.

For the $C_1$-$C_{10}$ cyanoalkyl groups, those groups wherein at least one hydrogen atom of the above-indicated alkyl groups is substituted with a cyano group are mentioned.

For the condensed heteroaryl group, mention is made of thieno[3,4-b]pyrazin-5-yl, furo[3,4-b]pyrazin-5-yl, 6H-pyrolo[3,4-b]pyrazin-5-yl, and the like.

The $C_1$-$C_{10}$ alkoxy groups may be linear, branched or cyclic and include, for example, methoxy, ethoxy, n-propoxy, i-propoxy, n-butoxy, i-butoxy, s-butoxy, t-butoxy, n-pentyloxy, n-hexyloxy, 1,1-dimethylpropoxy, 1,2-dimethylpropoxy, 2,2-dimethylpropoxy, 1-ethylpropoxy, 1,1,2-trimethylpropoxy, 1,2,2-trimethylpropoxy, 1-ethyl-1-methylpropoxy, 1-ethyl-2-methylpropoxy, 1-methylbutoxy, 2-methylbutoxy, 3-methylbutoxy, 1-ethylbutoxy, 2-ethylbutoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-methylpentyloxy, 2-methylpentyloxy, 3-methylpentyloxy, 4-methylpentyloxy and the like.

In the above-indicated groups, "n", "I", "S", and "t", respectively, mean normal, iso, secondary and tertiary.

Examples of the compounds indicated by the formulae (1a) to (1d) include those indicated below although not limitative.

[Chemical Formula 29]

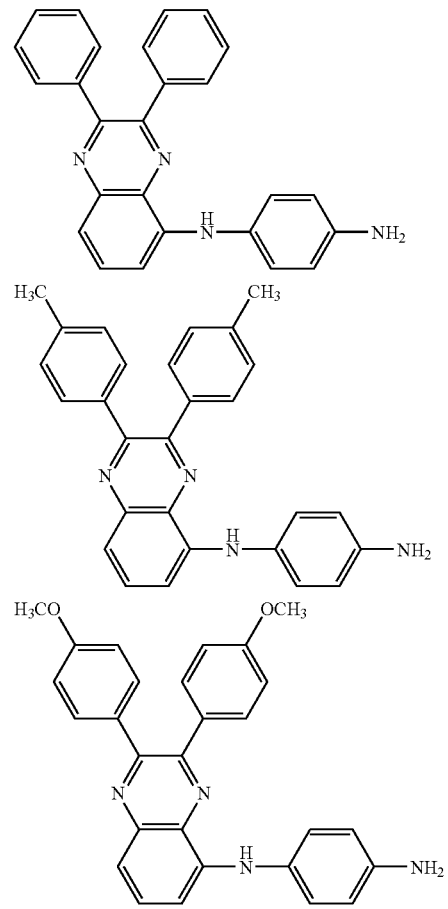

-continued
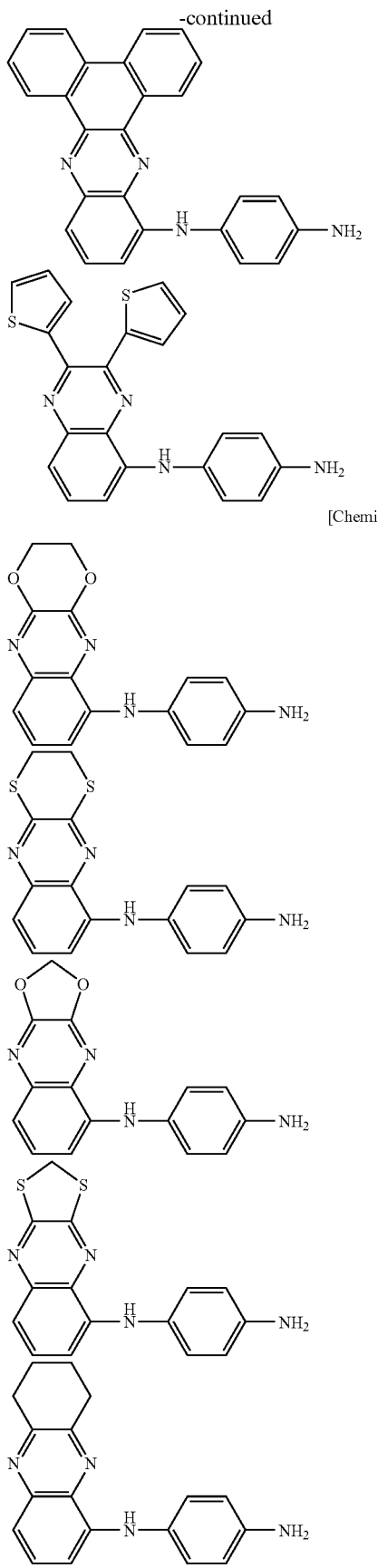
[Chemical Formula 30]
-continued
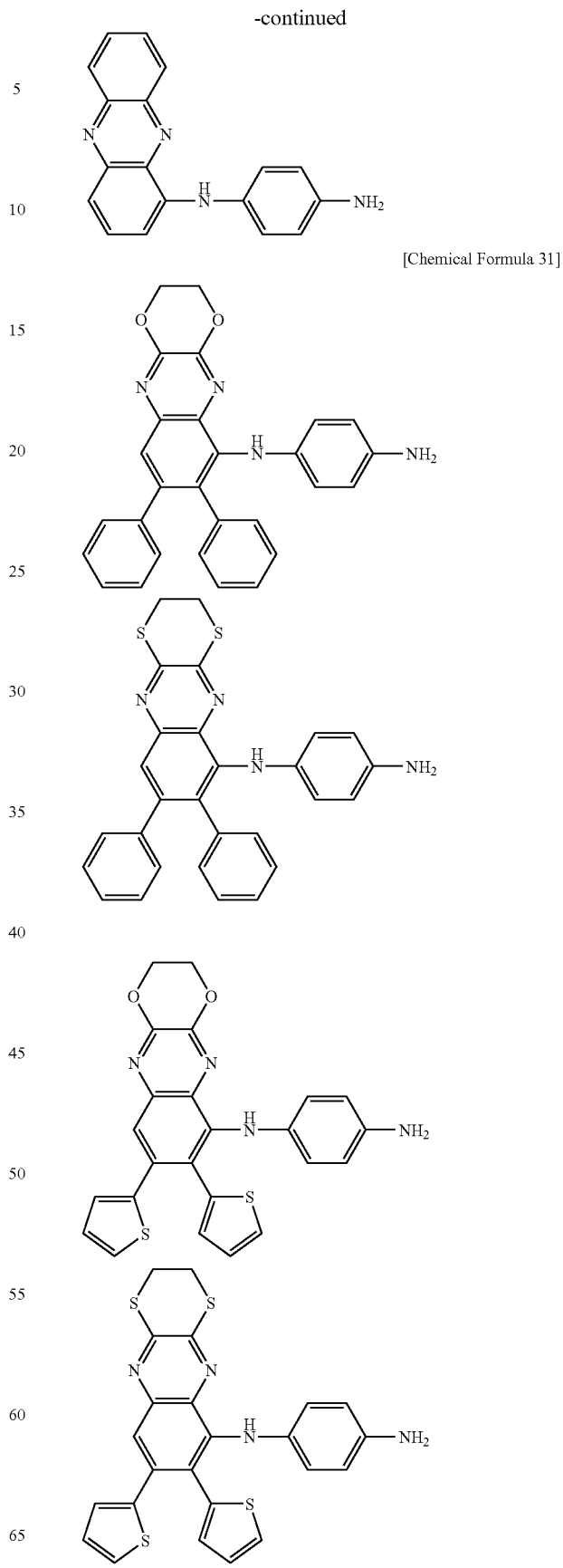
[Chemical Formula 31]

-continued
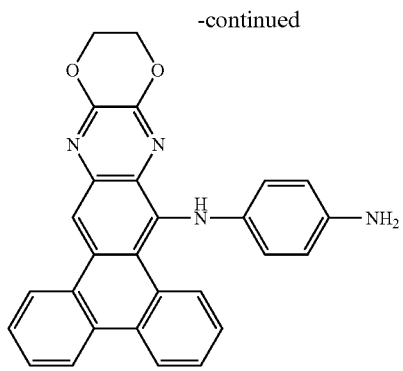
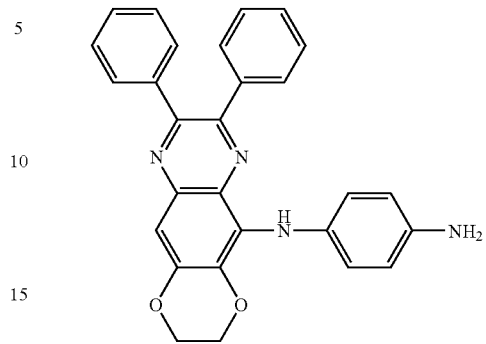
[Chemical Formula 33]
[Chemical Formula 32]
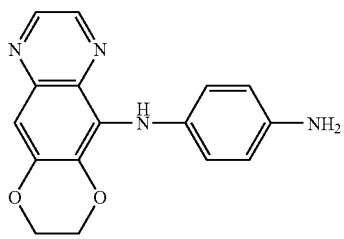
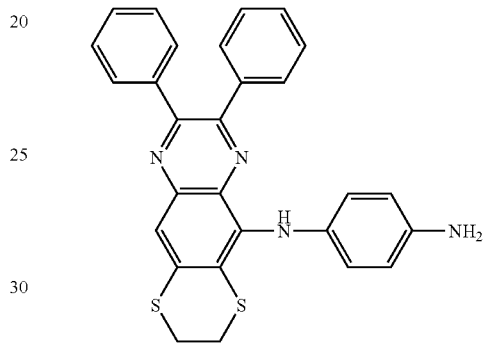
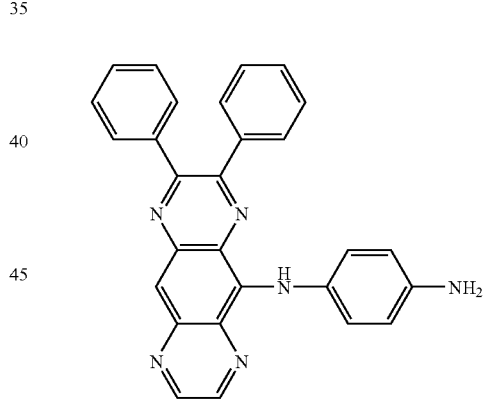
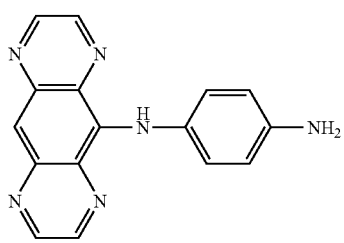
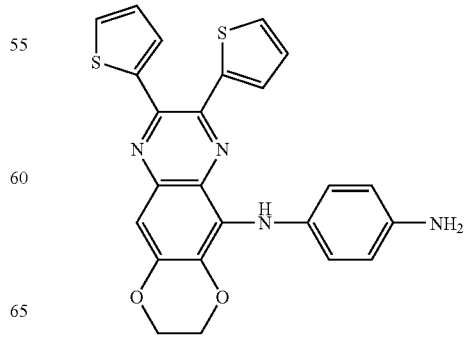

-continued

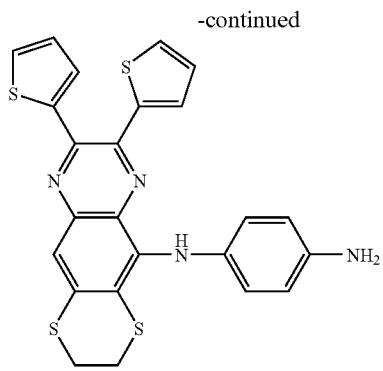

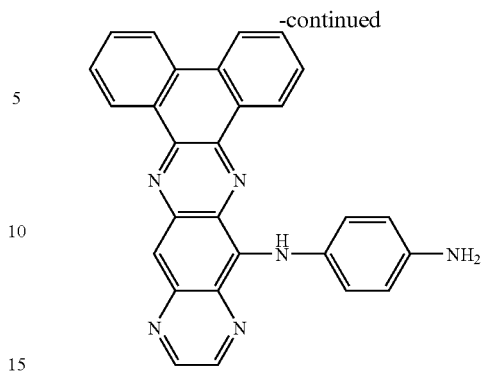

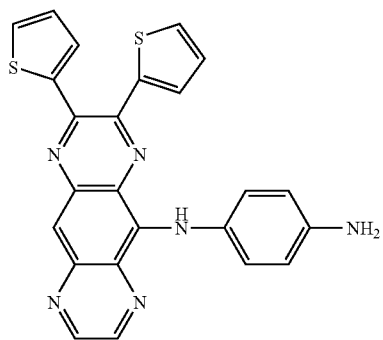

[Chemical Formula 34]

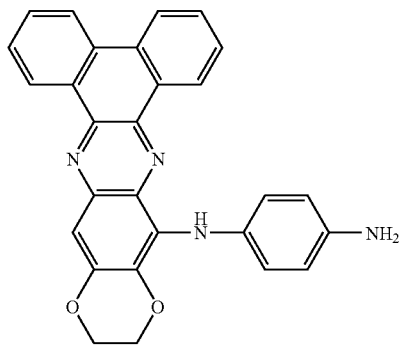

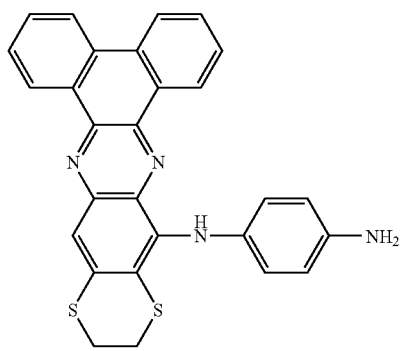

Next, as to the process of synthesizing the compound represented by the formulae (1a) to (1d), (18a) to (18d), the process of synthesizing the compound of the formula (1a) is described as an example of representative. This compound can be prepared from a starting 5-aminoquinoxaline compound represented by the following formula (19)

[Chemical Formula 35]

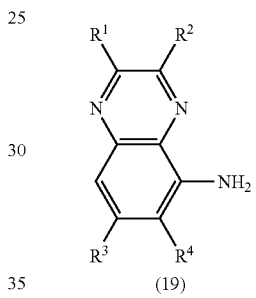

(19)

wherein $R^1$ to $R^4$, respectively, have the same meanings as defined in the formula (1a).

Although limitation is not placed on a specific manner of synthesis, there may be used processes set forth in Journal of the Chemical Society Perkin Transactions I (J. Chem. Soc. Perkin Trans. I) 1988, pp/1331 to 1335, and also in Chemistry Letters (Chem. Lett.) 1997, pp. 1185-1186.

For example, a corresponding 5-aminoquinoxaline compound is dissolved in an appropriate solvent and is reacted with nitrofluorobenzene in the presence of an appropriate base at room temperature, followed by hydrogenation reaction in the presence of Pd/C to obtain an intended product wherein a phenyl ring has been introduced at the position of $R^5$. An intended compound having a thienyl group at $R^6$ can be prepared by dissolving a 5-aminoquinoxaline compound in an appropriate solvent, adding catalytic amounts of $Pd_2(dba)_3$ and BINAP and reacting with 2-bromothiophene in the presence of an appropriate base.

It will be noted that the synthesis of the 5-aminoquinoxalien compound of the above formula (19) is not limitative, and there may be used processes, for example, set forth in Journal of American Chemical Society (J. Am. Chem. Soc.) 1957, vol. 79, pp/2245 to 2248 and Journal of Organic Chemistry (J. Org. Chem.) 1966, vol. 31, pp/3384 to 3390.

It will be noted that the synthesis of the polyaminoquinoxaline compound of the above formula (18a) is not limitative, and can be prepared by polymerizing the aminoquinoxaline compound of the formula (1a) by any arbitrary procedure. Such polymerizing procedures may include chemical oxidation polymerization, electrolytic oxidation polymerization, catalytic polymerization and the like. In most cases, in view of the fact that a polymer can be formed on an electrode surface, chemical oxidation polymerization and electrolytic oxidation polymerization are preferred, of which the electrolytic oxidation polymerization is more preferred.

The oxidizing agent used for the chemical oxidation polymerization is not critical and includes ammonium persulfate, tetraammonium peroxide, iron chloride, cerium sulfate and the like.

A specific procedure for the electrolytic oxidation polymerization is as follows: an oxidizing agent is added, for example, to a monomer of the formula (1a) and well agitated, to which an organic solvent is added thereto so as to make a uniform solution; and the resulting solution is subjected to electrolytic polymerization by use of a three-electrode beaker-shaped cell equipped with a platinum mesh counter electrode and the like.

The electrolytic polymerization is carried out, for example, according to an electrochemical measuring system using, as a test electrode substrate, a platinum plate whose surface is abraded with an emery paper and, as a reference electrode, $Ag/Ag^+$. For a more specific procedure of electrolytic polymerization, a potential scanning process and a constant potential process may be used, for example. Thus the intended high molecular compound is precipitated on the electrode in film form.

The oxidizing agents used for the electrolytic oxidation polymerization include hydrochloric acid, sulfuric acid, perchloric acid, trifluoromethanesulfonic acid, para-toluenesulfonic acid and the like, of which perchloric acid is preferred.

Examples of the organic solvents include N,N-dimethylformamide, tetrahydrofuran, acetonitrile, dichloromethane, dimethylsulfoxide, methanol, ethanol and the like, of which N,N-dimethylformamide is preferred.

While making use of their good characteristics, the compounds of the invention are applicable to as a film, an electrochromic element, a semiconductor, a solar cell, an organic electroluminescent element, an active substance of a non-linear material. The compounds exhibit electric conductivity on their own and can be utilized as an n-type semiconductor by applying a reducing agent to or electrochemically doping the compound of the invention. When the compound of the invention is shaped as a film or other molded articles, additives such as heat stabilizers, light stabilizers, fillers or reinforcing agents may be added in an appropriate manner.

EXAMPLES

The invention is more particularly described in detail by way of examples, which should not be construed as limiting the invention thereto. NMR spectra were measured by JNM-ECP200 (made by JEOL, Ltd.), and mass spectra were measured by Voyager DE Pro (made by Applied Biosystems) in the following Examples.

Synthetic Example 1

Synthesis of 2,3-dihydroxy-5-aminoquinoxaline

Prepared according to the following procedures (1) to (3).

(1) Synthesis of 2,3-diaminonitrobenzene

[Chemical Formula 36]

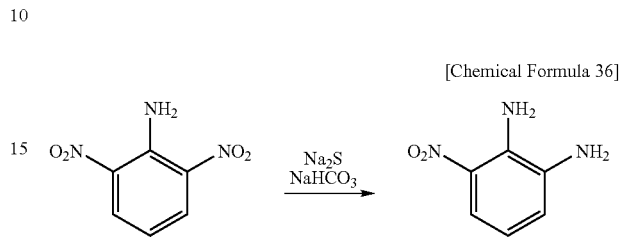

14 g of commercially available 1-amino-2,5-dinitrobenzene was dissolved in 225 ml of methanol, to which a solution of 60 g of sodium sulfide and 21 g of sodium hydrogen carbonate dissolved in 240 g of water was added by use of a dropping funnel while keeping the reaction temperature at 60° C. After completion of the addition, agitation was continued at 60° C. for 1 hour. After completion of the reaction, the mixture was cooled down to room temperature and filtered.

m/z: (FD+) 153 (calculated 153. 1396)

$^1$H-NMR: 7.7228, 7.7203, 7.7026, 7.2433, 6.9245, 6.6209, 6.6063, 6.6038, 6.5886, 5.9210, 3.3978 ppm Yield: 7.79 g (66.5%)

Reddish brown fine crystals

Melting point: 140° C.

(2) Synthesis of 2,3-dihydroxy-5-nitroquinoxaline

[Chemical Formula 37]

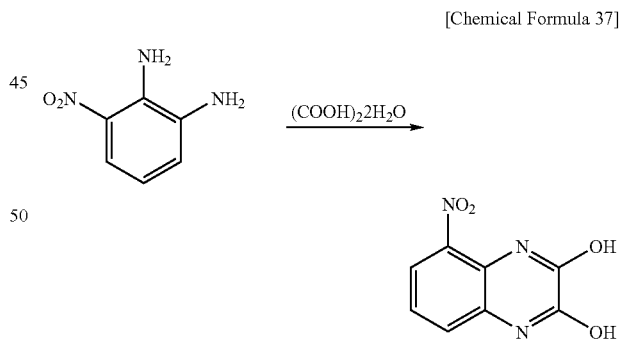

4 g (26.12 mmol) of 2,3-diaminonitrobenzene and 6.59 g (52.24 mmol) of commercially available oxalic dehydrate were dissolved in 50% acetic acid, followed by reaction at a boiling point thereof for 3 hours in a stream of argon. After completion of the reaction, the mixture was cooled down to room temperature and the resulting precipitated crystals were filtered.

Yield: 3.01 g (55.6%)

Yellow fine crystals m/z: 207 (calculated: 207.144)

(3) Synthesis of 2,3-dihydroxy-5-aminoquinoxaline

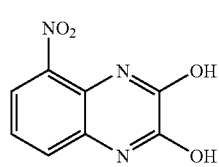  [Chemical Formula 38]

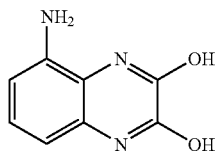

2.0 g of 2,3-dihydroxy-5-nitroquinoxaline was dissolved in 100 g of a 1:1 methanol and dioxane solvent, after which the reaction system was well purged with argon, followed by further addition of 1 g of 5% Pd/C (hydrous). Thereafter, the system was purged with hydrogen, followed by reaction at room temperature for 20 hours. After completion of the reaction, the reaction product was dispersed in a solution of 6.00 g of potassium carbonate in 130 ml of water and then dissolved therein. 35% hydrochloric acid was gradually added to the solution obtained after filtration thereby obtaining a precipitate.

Yield: 1.10 g
Light yellow fine crystals
m/z: (FD+) 177 (calculated: 177.1616)
$^{13}$C-NMR: 155.8030, 155.6504, 135.9570, 126.8390, 124.1303, 112.3265, 109.6025, 103.8418 ppm

Synthetic Example 2

Synthesis of 2,3-diphenyl-5-aminoquinoxaline

Prepared according to the following procedure (1) and (2).

(1) Synthesis of 2,3-diphenyl-5-nitroquinoxaline

[Chemical Formula 39]

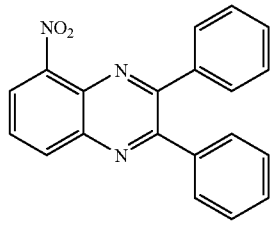

1.53 g (10 mmol) of 2,3-diaminonitrobenzene and 2.00 g (9.6 mmol) of benzyl were placed in four-necked flask, to which 30 g of a solvent of acetic acid and methanol at a mixing ratio of 1:1 was added for dissolution. Subsequently, the mixture was reacted at a reaction temperature of 70° C. for 2 hours. After the reaction, the solvent was removed and the resulting product was extracted with a silica gel column (ethyl acetate:hexane=1:1).

Yield: 2.11 g
Yellow fine crystals
m/z: 327 (calculated: 327.24)

(2) Synthesis of 2,3-diphenyl-5-aminoquinoxaline

[Chemical Formula 40]

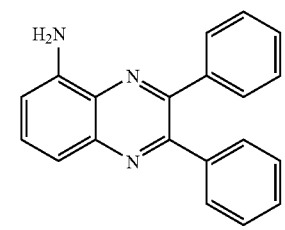

1.04 g of 2,3-diphenyl-5-nitroquinoxaline was dissolved in 30 g of dioxane, followed by purging with argon and further addition of 0.5 g of 5% Pd/C (hydrous). After sufficient purging with argon again, hydrogen was added and reacted at room temperature for 30 hours. After completion of the reaction, the reaction mixture was filtered and the solvent was removed, followed by isolation and purification with a silica gel column (ethyl acetate:hexane=1:3).

Yield: 0.73 g
Yellow fine crystals
m/z: 297 (calculated M: 297.36)
$^{13}$C-NMR: 153.6055, 150.1185, 144.2280, 141.9619, 139.4516, 139.3524, 131.1348, 130.0894, 129.9368, 128.7694, 128.6473, 128.3497, 128.1743, 117.2098, 110.2511 ppm

Synthetic Example 3

Synthesis of 2,3-di(4-methylphenyl)-5-aminoquinoxaline

Prepared according to the following procedures (1) and (2).

(1) Synthesis of 2,3-di(4-methylphenyl)-5-nitroquinoxaline

[Chemical Formula 41]

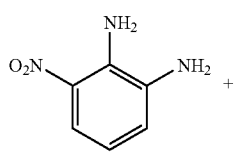

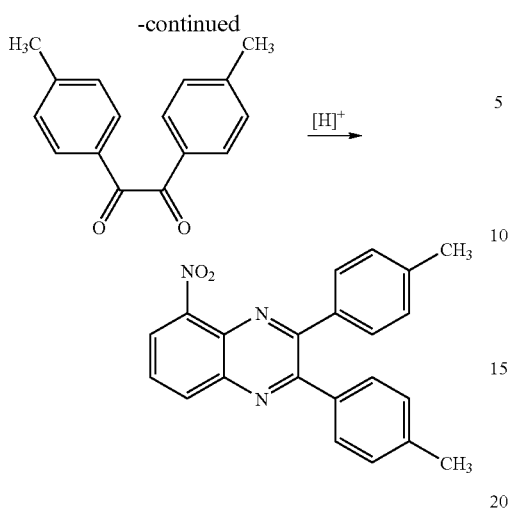

1.84 g (12 mmol) of 2,3-diaminonitrobenzene and 2.38 g (10 mmol) of 4,4'-dimethylbenzyl were dissolved in 40 g of a mixed solvent of acetic acid and methanol (1:1) and reacted at a reaction temperature of 80° C. for 4 hours. After completion of the reaction, the solvent was removed and the resulting reaction product was extracted by means of a silica gel column.

Yield: 1.30 g
Yellow fine crystals
m/z: 355 (calculated: 355.39)
$^{13}$C-NMR: 154.8950, 154.8339, 147.0894, 140.7563, 140.1307, 139.8636, 135.5984, 135.1253, 133.7061, 133.2254, 130.2725, 129.7003, 129.3188, 129.1204, 128.4108, 127.7470, 124, 2142 ppm (2) Synthesis of 2,3-di(4-methylphenyl)-5-aminoquinoxaline

[Chemical Formula 42]

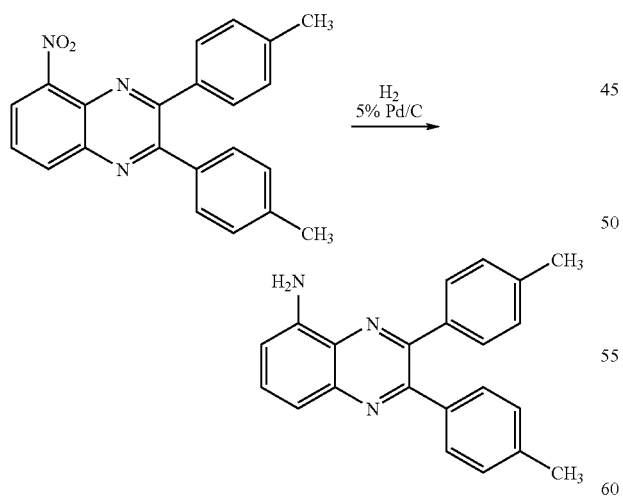

2.02 g of 2,3-di(4-methylphenyl)-5-nitroquinoxaline was dissolved in 30 g of dioxane, followed by purging with argon and adding 0.6 g of 5% Pd/C (hydrous). After purging with argon again, the system was purged with hydrogen for reaction at room temperature for 18 hours. After completion of the reaction, the system was filtered. The filtration residue was washed with acetone and then with dioxane and re-filtered. The solvent was removed from the resulting filtrate, followed by extracting a reaction product by use of a silica gel column.

Yield: 1.36 g
Yellow fine crystals
m/z: 325 (calculated M: 325.14)
$^{13}$C-NMR: 153.6131, 150.1643, 144.0907, 141.8551, 138.6581, 138.5894, 136.7047, 136.6666, 131.2721, 130.7761, 129.9292, 129.7766, 129.0365, 128.9815, 117.2403, 110.0603 ppm Synthetic Example 4

Synthesis of 2,3-di(4-methoxyphenyl)-5-aminoquinoxaline

Prepared according to the following procedures (1) and (2).

(1) Synthesis of 2,3-(4-dimethoxyphenyl)-5-nitroquinoxaline

[Chemical Formula 43]

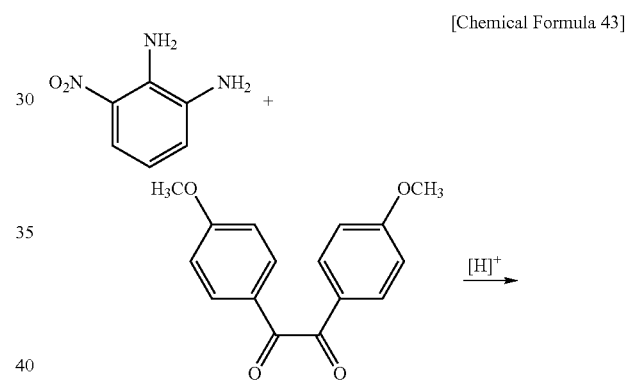

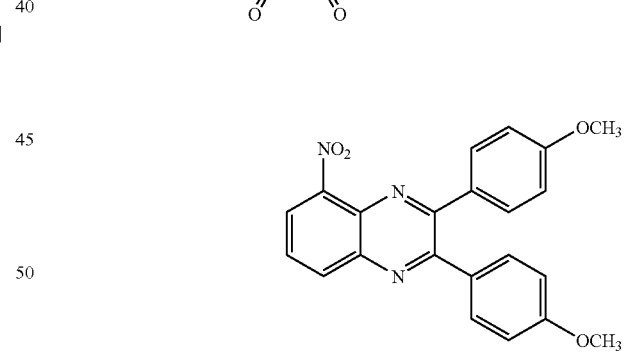

1.54 g (10 mmol) of 2,3-diaminonitrobenzene and 2.25 g (8.3 mmol) of 4,4'-dimethoxybenzyl were dissolved in 100 g of a mixed solvent (acetic acid:methanol=1:1) and reacted at room temperature for 20 hours, and, after completion of the reaction, filtered. The resulting filtration residue was washed with acetone and dioxane, and again filtered. The solvent was removed from the resulting filtrate, and a reaction product was extracted by means of a silica gel column.

Yield: 1.24 g
Yellow fine crystals
m/z: 387 (calculated M: 387.39)

$^{13}$C-NMR: 161.0983, 160.9075, 154.3303, 154.2464, 146.9520, 140.6495, 133.5993, 133.1415, 131.9207, 130.8448, 130.4099, 127.5104, 124.0998, 114.1043, 113.8830 ppm (2) Synthesis of 2,3-di(4-methoxyphenyl)-5-aminoquinoxaline

[Chemical Formula 44]

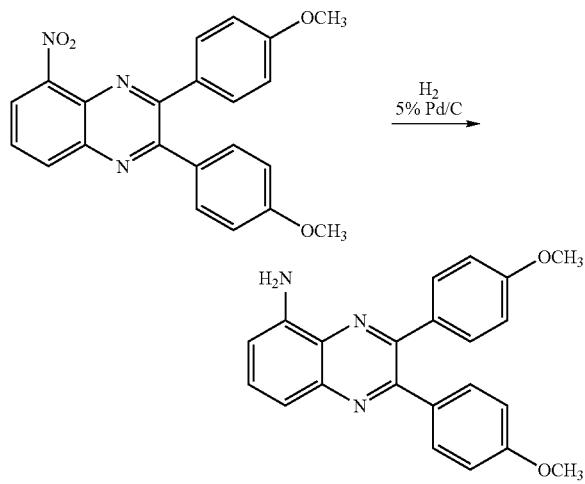

0.55 g of 2,3-(4-dimethoxyphenyl)-5-nitroquinoxaline was dissolved in 30 g of dioxane, followed by purging well with argon, adding 0.5 g of 5% Pd/C (hydrous) and purging satisfactorily with argon again. This system was purged with hydrogen gas and reacted at room temperature for 24 hours. After completion of the reaction, the system was filtered.

The resulting filtration residue was washed with acetone and then with dioxane and filtered again. The solvent was removed from the resulting filtrate and a reaction product was extracted with a silica gel column.

Yield: 0.37 g
Yellow fine crystals
m/z: 325 (calculated: 325.43)
$^{13}$C-NMR: 160.1369, 160.0606, 153.1324, 149.7370, 144.0144, 141.7483, 131.3942, 131.2874, 130.6235, 117.1640, 113.8296, 113.6618, 110.0145, 55.3828 ppm Synthetic Example 5

Synthesis of 2,3-di(4-bromophenyl)-5-aminoquinoxaline

Prepared according to the following procedures (1) and (2).

(1) Synthesis of 2,3-di(4-bromophenyl)-5-nitroquinoxaline

[Chemical Formula 45]

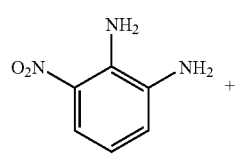

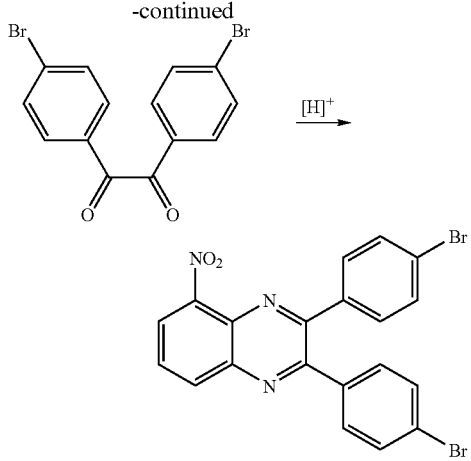

1.53 g (10 mmol) of 2,3-diaminonitrobenzene and 3.68 g (10 mmol) of 4,4'-dibromobenzyl were dissolved in 80 g of a mixed solvent of acetic acid and methanol (1:1) and reacted at a reaction temperature of 70° C. for 30 hours. After completion of the reaction, the solvent was removed and a reaction product was extracted by means of a silica gel column.

Yield: 1.89 g
Yellow fine crystals
m/z: 485 (calculated: 485.12)
$^{13}$C-NMR: 153.4453, 153.3613, 147.0065, 140.7945, 136.8116, 136.3766, 133.7824, 133.2635, 132.0504, 131.8749, 131.8215, 131.3789, 128.5787, 124.9849, 124.8780, 124.7102 ppm (2) Synthesis of 2,3-di(4-bromophenyl)-5-aminoquinoxaline

[Chemical Formula 46]

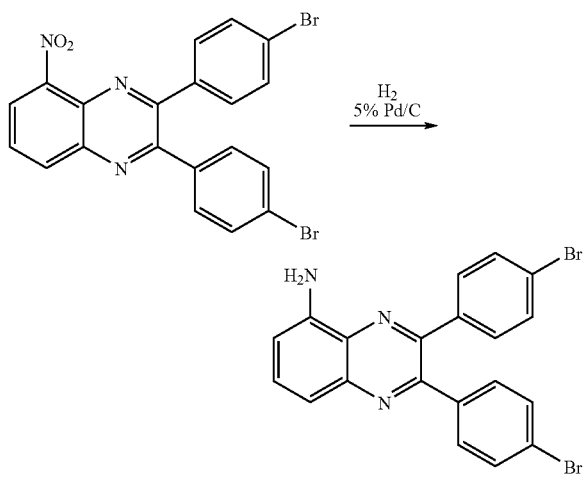

1.01 g (2.1 mmol) of 2,3-di(4-bromophenyl)-5-nitro-quinoxaline was dissolved in 30 g of dioxane, followed by purging well with argon, adding 0.3 g of 5% Pd/C (hydrous) and purging well with argon again. This system was purged with a hydrogen gas and reacted at room temperature for 24 hours. After completion of the reaction, the system was filtered. The resulting filtration residue was washed with acetone and then with dioxane and filtered again. The solvent was removed from the resulting filtrate and a reaction product was extracted with a silica gel column.

Yield: 0.66 g

Yellow fine crystals m/z: 455 (calculated: 455.12)

$^{13}$C-NMR: 151.966, 148.493, 144.065, 141.897, 137.920, 137.820, 135.042, 131.706, 131.637, 131.492, 131.400, 131.248, 123.514, 123.377, 117.064, 110.452 ppm Synthetic Example 6

Synthesis of 2,3-dithianyl-5-aminoquinoxaline

Prepared according to the following procedures (1) and (2).

(1) Synthesis of 2,3-dithianyl-5-nitroquinoxaline

[Chemical Formula 47]

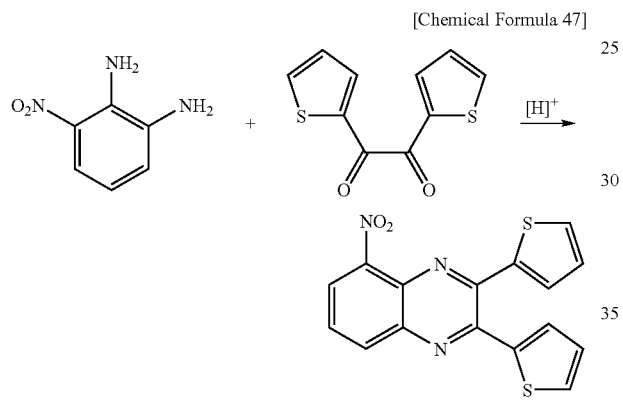

0.022 g (0.099 mmol) of 2,3-diaminonitrobenzene and 0.01938 g (0.198 mmol) were dissolved in 3 g of a mixed solvent of acetic acid and methanol (1:1) and reacted at a reaction temperature of 70° C. for 30 hours. After completion of the reaction, the solvent was removed and the resulting reaction produced was extracted by means of a silica gel column.

Yield: 0.04 g

Yellow fine crystals m/z: 339 (calculated: 339.40)

(2) Synthesis of 2,3-dithienyl-5-aminoquinoxaline

[Chemical Formula 48]

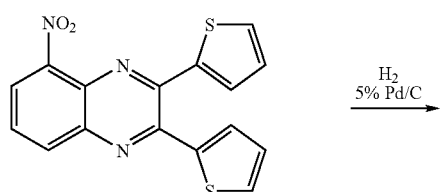

-continued

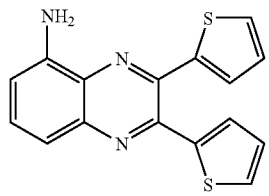

1.01 g (3.0 mmol) of 2,3-dithienyl-5-nitroquinoxaline was dissolved in 30 g of dioxane and the system was fully purged with argon. Thereafter, 0.3 g of 5% Pd/C (hydrous) was added, followed by purging satisfactorily with argon again. This system was purged with a hydrogen gas and reacted at room temperature for 24 hours. After completion of the reaction, the system was filtered. The resulting filtration residue was washed with acetone and then with dioxane, and was filtered again. The solvent was removed from the resulting filtrate, and a reaction product was extracted with a silica gel column.

Yield: 0.40 g

Yellowish brown fine crystals m/z: 309 (calculated: 309.42)

$^{13}$C-NMR: 146.569, 143.752, 142.111, 141.546, 141.233, 131.232, 130.614, 129.064, 128.820, 128.553, 128.469, 127.530, 127.461, 116.911, 110.422, 99.902 ppm Synthetic Example 7

Synthesis of 10-aminodibenzo(A,C)phenazine

Prepared according to the following procedures (1) and (2).

(1) Synthesis of 1,2,3-triaminobenzene

[Chemical Formula 49]

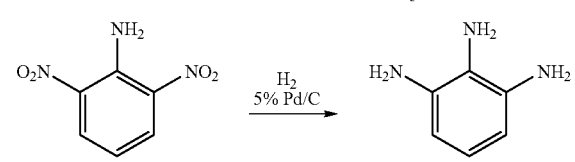

15.0 g (82 mmol) of 2,6-dinitroaniline was dissolved in 150 g of THF and the reaction system was satisfactorily purged with nitrogen, to which 7.6 g of 5% Pd/C (hydrous) was added. Thereafter, the system was purged with hydrogen, followed by reaction at room temperature for 15 hours. After completion of the reaction, the reaction solution was filtered to remove Pd therefrom, and the resulting filtrate was condensed as it is to obtain the intended product. The thus obtained product was instable and was used as it is in a subsequent reaction.

(2) Synthesis of 10-aminodibenzo(A,C)phenazine

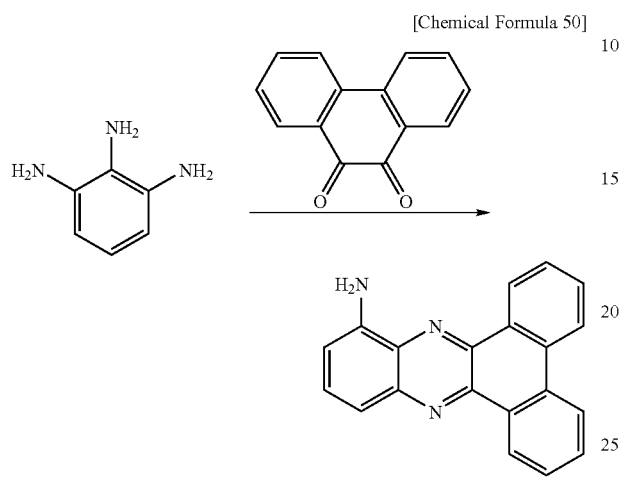

[Chemical Formula 50]

10.1 g (82 mmol) of 1,2,3-triaminobenzene and 4.6 g (70 mmol) of 9,10-phenanthrenequinone were placed in a four-necked flask, to which 350 g of a solvent of acetic acid and methanol at 1:1 was added for dissolution, followed by reaction at a reaction temperature of 70° C. for 2 hours. After the reaction, the solvent was removed and the resulting product was washed with methanol to obtain the intended product.

Yield: 17.1 g

Ocher solid m/z: 295 (calculated: 295.11)

$^{13}$C-NMR: 146.932, 144.145, 143.084, 139.740, 133.473, 133.007, 132.656, 132.213, 131.602, 131.488, 130.847, 130.473, 128.465, 126.869, 126.831, 126.663, 123.900, 116.243, 108.647 ppm Example 1

Synthesis of 2,3-diphenyl-5-(4-aminophenyl)aminoquinoxaline

Prepared according to the following procedures (1) and (2).

(1) Synthesis of 2,3-diphenyl-5-(4-nitrophenyl)aminoquinoxaline

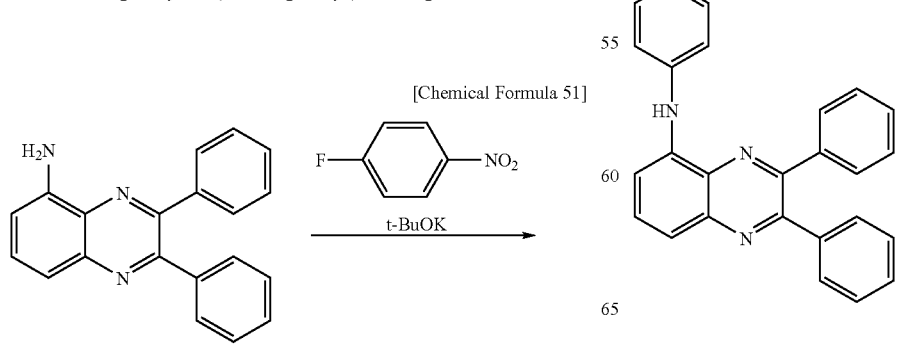

[Chemical Formula 51]

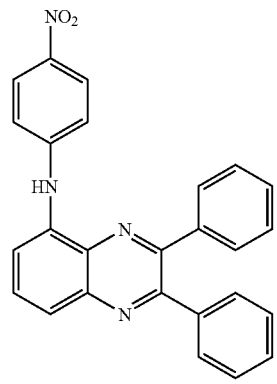

While agitating 4.0 g (13.4 mmol) of 2,3-diphenyl-5-aminoquinoxaline, 2.1 g (14.9 mmol) of 4-fluoronitrobenzene and 100 ml of dimethylsulfoxide, 5.0 g (44.6 mmol) of potassium t-butoxide was gently added thereto. After completion of the addition, the reaction container was purged with nitrogen, followed by agitation at room temperature for 24 hours. After completion of the reaction, 100 ml of water was added to the container while cooling, and an organic phase was extracted with a chloroform solvent, followed by evaporation of the solvent for concentration to obtain the intended product.

Yield: 5.4 g (2) Synthesis of 2,3-diphenyl-5-(4-aminophenyl)aminoquinoxaline

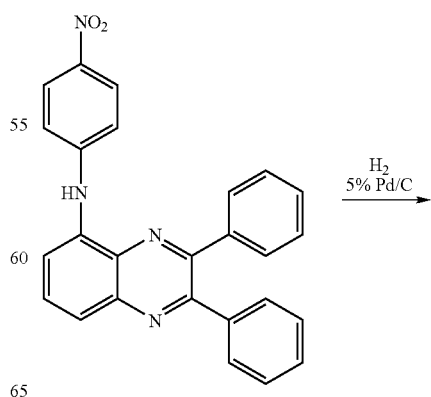

[Chemical Formula 52]

-continued

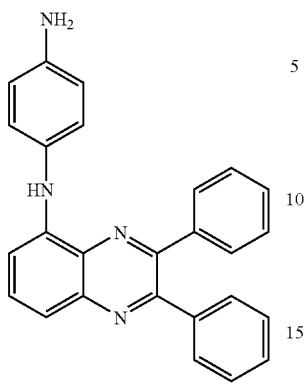

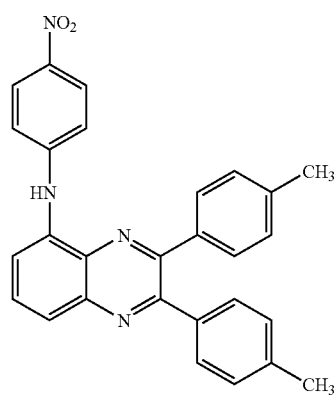

5.4 g (2.9 mmol) of 2,3-diphenyl-5-(4-nitrophenyl)-aminoquinoxaline was dissolved in 100 ml of tetrahydrofuran, and the reaction container was purged with nitrogen. Thereafter, 5.0 g of 5% Pd/C (hydrous) was added to the system, which was satisfactorily purged with nitrogen again. This system was subsequently purged with hydrogen gas and reacted at room temperature for 10 hours. After completion of the reaction, the system was filtered. The resulting filtration residue was washed with tetrahydrofuran and filtered again. The solvent was removed from the resulting filtrate, after which a reaction product was recrystallized from a mixed solvent of tetrahydrofuran and heptane.

Yield: 3.9 g

Orange solid m/z: 388 (calculated: 388.17)

$^{13}$C-NMR: 153.597, 149.658, 142.978, 142.887, 142.009, 139.306, 139.199, 132.290, 131.283, 130.008, 129.825, 128.680, 128.588, 128.267, 128.130, 124.794, 116.198, 116.114, 106.648 ppm Example 2

Synthesis of 2,3-di(4-methylphenyl)-5-(4-aminophenyl)-aminoquinoxaline

Prepared according to the following procedures (1) and (2).

(1) Synthesis of 2,3-di(4-methylphenyl)-5-(4-nitrophenyl)-aminoquinoxaline

While agitating 3.0 g (9.2 mmol) of 2,3-di(4-methylphenyl)-5-aminoquinoxaline, 1.4 g (9.9 mmol) of 4-fluoronitrobenzene and 100 ml of dimethylsulfoxide, 3.4 g (30.3 mmol) of potassium t-butoxide was gently added thereto. After completion of the addition, the reaction container was purged with nitrogen, followed by agitation at room temperature for 20 hours. After completion of the reaction, 100 ml of water was added to the container while cooling, and an organic phase was extracted with a chloroform solvent, followed by evaporation of the solvent for concentration to obtain the intended product.

Yield: 5.9 g m/z: 446 (calculated: 446.17)

(2) Synthesis of 2,3-di(4-methylphenyl)-5-(4-aminophenyl)-aminoquinoxaline

[Chemical Formula 54]

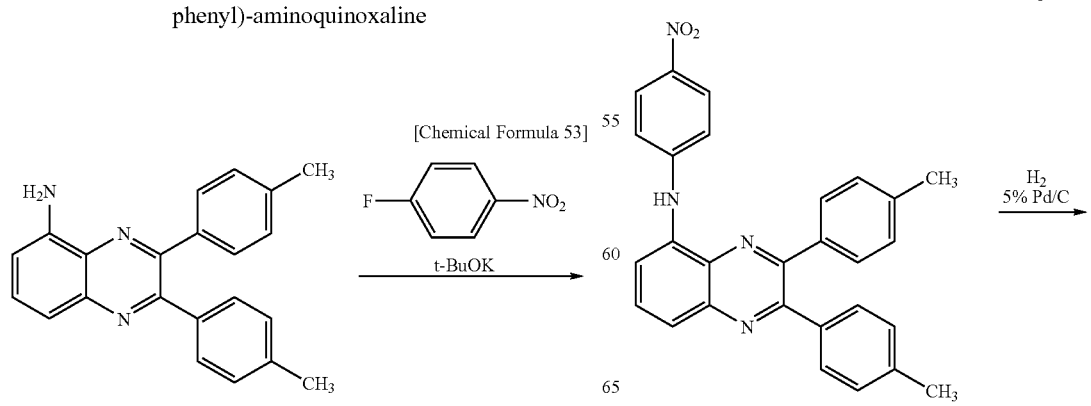

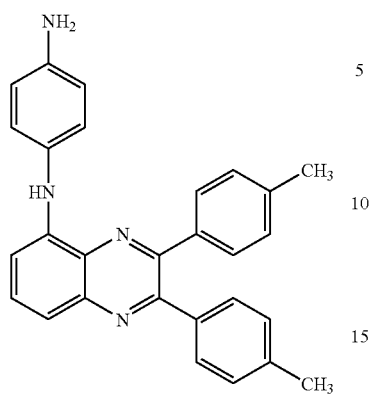

5.9 g (13.2 mmol) of 2,3-di(4-methylphenyl)-5-(4-nitrophenyl)aminoquinoxaline was dissolved in 70 ml of tetrahydrofuran, and the reaction container was purged with nitrogen. Thereafter, 2.0 g of 5% Pd/C (hydrous) was added to the system, which was satisfactorily purged with nitrogen again. This system was subsequently purged with hydrogen gas and reacted at room temperature for 13 hours. After completion of the reaction, the system was filtered. The resulting filtration residue was washed with tetrahydrofuran and filtered again. The solvent was removed from the resulting filtrate, after which a reaction product was extracted by means of a silica gel column.

Yield: 1.1 g

Orange solid m/z: 416 (calculated: 416.20)

$^{13}$C-NMR: 153.605, 149.711, 142.719, 141.917, 138.573, 136.543, 132.542, 130.977, 129.863, 129.703, 128.970, 128.870, 124.664, 116.198, 106.480, 21.352 ppm Example 3

Synthesis of 2,3-di(4-methoxylphenyl)-5-(4-aminophenyl)-aminoquinoxaline

Prepared according to the following procedures (1) and (2).

(1) Synthesis of 2,3-di(4-methoxylphenyl)-5-(4-nitrophenyl)-aminoquinoxaline

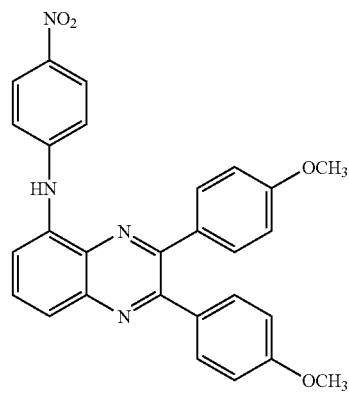

While agitating 5.0 g (14.0 mmol) of 2,3-di(4-methoxyphenyl)-5-aminoquinoxaline, 2.4 g (17.0 mmol) of 4-fluoronitrobenzene and 120 ml of dimethylsulfoxide, 5.7 g (50.8 mmol) of potassium t-butoxide was gently added thereto. After completion of the addition, the reaction container was purged with nitrogen, followed by agitation at room temperature for 8 hours. After completion of the reaction, 100 ml of water was added to the container while cooling, and an organic phase was extracted with a chloroform solvent, followed by evaporation of the solvent for concentration to obtain the intended product.

Yield: 8.3 g

Brown solid (2) Synthesis of 2,3-di(4-methoxyphenyl)-5-(4-aminophenyl)-aminoquinoxaline

[Chemical Formula 55]

[Chemical Formula 56]

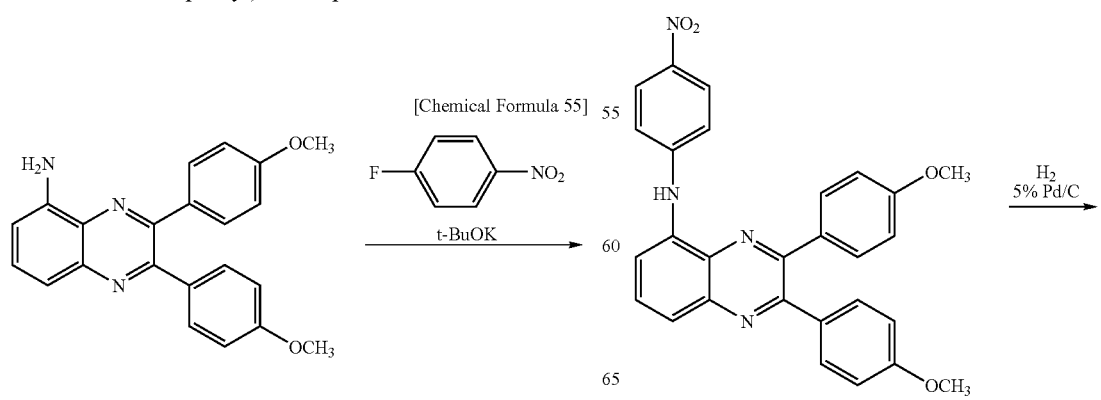

-continued

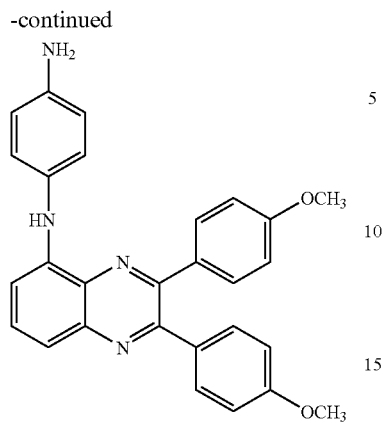

8.3 g (17.3 mmol) of 2,3-di(4-methoxyphenyl)-5-(4-nitrophenyl)aminoquinoxaline was dissolved in 100 ml of tetrahydrofuran, and the reaction container was purged with nitrogen. Thereafter, 5 g of 5% Pd/C (hydrous) was added to the system, which was satisfactorily purged with nitrogen again. This system was subsequently purged with hydrogen gas and reacted at room temperature for 10 hours. After completion of the reaction, the system was filtered. The resulting filtration residue was washed with tetrahydrofuran and filtered again. The solvent was removed from the resulting filtrate, after which a reaction product was recrystallized from hexane.

Yield: 4.5 g
Orange solid
m/z: 448 (calculated: 448.19)
$^{13}$C-NMR: 163.766, 159.994, 153.131, 148.872, 142.940, 142.688, 141.803, 132.420, 131.947, 131.329, 131.206, 130.779, 124.725, 116.076, 113.755, 113.625, 106.411, 98.953. 55.324 ppm

Example 4

Synthesis of 2,3-di(2-thienyl)-5-(4-aminophenyl)aminoquinoxaline

Prepared according to the following procedures (1) and (2).

Synthesis of 2,3-di(2-thienyl)-5-(4-nitrophenyl)-aminoquinoxaline

[Chemical Formula 57]

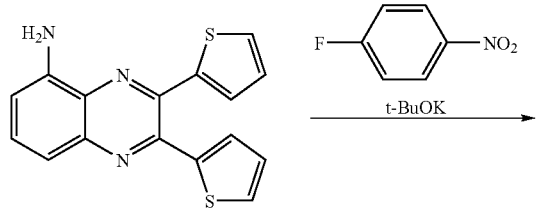

-continued

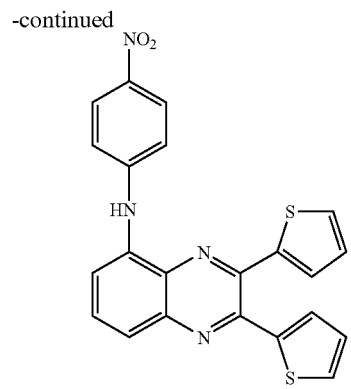

While agitating 3.1 g (9.9 mmol) of 2,3-di(2-thienyl)-5-aminoquinoxaline, 1.4 g (9.9 mmol) of 4-fluoronitrobenzene and 15 g of dimethylsulfoxide, 3.3 g (29.6 mmol) of potassium t-butoxide was gently added thereto. After completion of the addition, the reaction container was purged with nitrogen, followed by agitation at room temperature for 14 hours. After completion of the reaction, 100 ml of water was added to the container while cooling, and the resulting compound was filtered, dried and purified with a silica gel column.

Yield: 2.6 g
Yellow solid (2) Synthesis of 2,3-di(2-thienyl)-5-(4-aminophenyl)-aminoquinoxaline

[Chemical Formula 58]

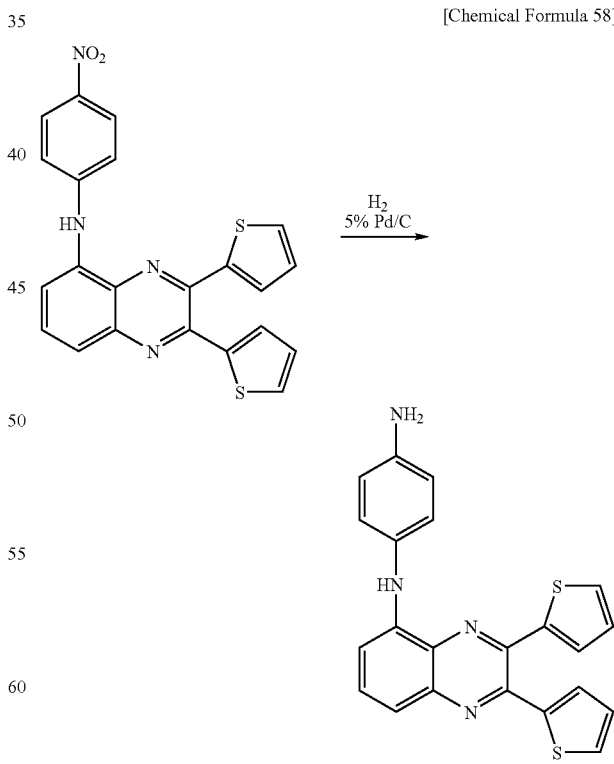

2.2 g (5.1 mmol) of 2,3-di(2-thienyl)-5-(4-nitro-phenyl) aminoquinoxaline was dissolved in 50 ml of tetrahydrofuran, and the reaction container was purged with nitrogen. Thereafter, 0.7 g of 5% Pd/C (hydrous) was added to the system, which was satisfactorily purged with nitrogen again. This system was subsequently purged with hydrogen and reacted at room temperature for 5 hours. After completion of the reaction, the system was filtered. The resulting filtration residue was washed with tetrahydrofuran and filtered again. The solvent was removed from the resulting filtrate, after which a reaction product was extracted with a silica gel column.

Yield: 1.9 g

Orange solid m/z: 399 (calculated: 400.08)

$^{13}$C-NMR: 146.665, 143.161, 143.009, 142.619, 142.009, 141.413, 132.084, 131.535, 130.443, 129.061, 128.840, 128.603, 128.473, 127.618, 127.512, 124.878, 116.068, 115.931, 106.930 ppm Example 5

Synthesis of N-4-aminophenyl-10-aminodibenzo(A,C)phenazine

Prepared according to the following procedures (1) to (2).

(1) Synthesis of N-4-nitrophenyl-10-aminobenzo(A,C)phenazine

[Chemical Formula 59]

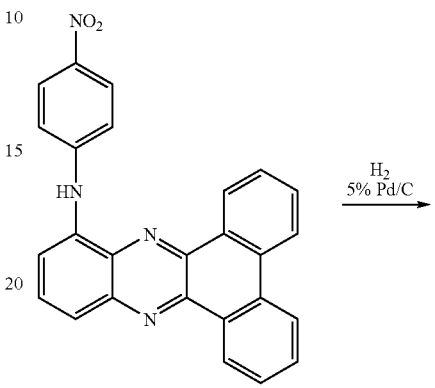

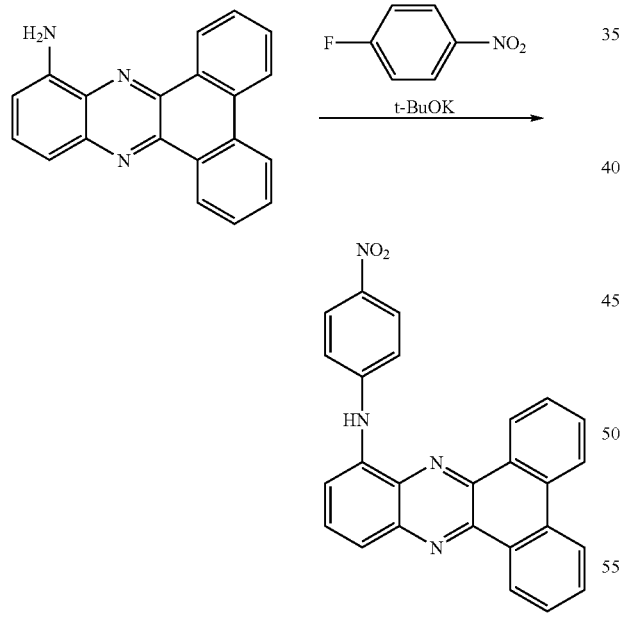

While agitating 10.0 g (34 mmol) of 10-aminodibenzo(A,C)phenazine, 4.8 g (34 mmol) of 4-fluoronitrobenzene and 500 ml of dimethylsulfoxide, 19.4 g (173 mmol) of potassium t-butoxide was gently added thereto. After completion of the addition, the reaction container was purged with nitrogen, followed by agitation at room temperature for 24 hours. After completion of the reaction, 500 ml of water was added to the container while cooling, and the reaction solution was filtered to obtain a filtration residue. The thus obtained residue was washed with methanol to obtain the intended product.

(2) Synthesis of N-4-aminophenyl-10-amnodibenzo(A,C)phenazine

[Chemical Formula 60]

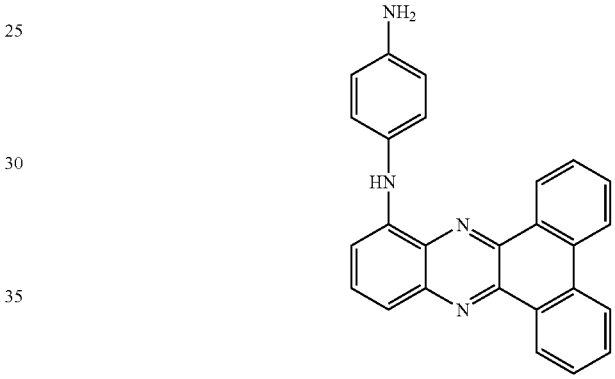

4.5 g (10.8 mmol) of N-4-nitrophenyl-10-aminodibenzo(A,C)phenazine was dissolved in 200 ml of tetrahydrofuran, and the reaction container was purged with nitrogen. Thereafter, 4.6 g of 5% Pd/C (hydrous) was added to the system, which was satisfactorily purged with nitrogen again. This system was subsequently purged with hydrogen gas and reacted at room temperature for 10 hours. After completion of the reaction, the system was filtered. The resulting filtration residue was washed with tetrahydrofuran and purified with a column to obtain the intended product.

Purple crystals m/z: 386 (calculated: 386.15)

$^{13}$C-NMR: 146.771, 145.183, 144.191, 143.244, 139.687, 133.526, 133.022, 132.671 132.236, 131.434, 131.389, 130.892, 130.587, 128.518, 126.877, 126.320, 125.892, 123.907, 116.319, 115.739, 105.960 ppm Example 6

Synthesis of poly{2,3-diphenyl-5-(4-aminophenyl)-aminoquinoxaline}

Using a three-electrode beaker cell equipped with a platinum mesh counter electrode, the intended product was synthesized by carrying out electrolytic oxidation according to a potential scanning procedure. More particularly, there was used a solution of 0.19 mg (0.5 mmol) of 2,3-diphenyl-5-(4-aminophenyl)aminoquinoxaline and 1.05 ml (11 mmol) of perchloric acid dissolved in 6.5 g of N,N-dimethylformamide. Electrolytic polymerization was conducted in such a way that a test electrode substrate used was a platinum sheet (1.0 cm² per surface) abraded with an emery paper on the surface thereof, a reference electrode was Ag/Ag⁺, and an electrochemical measuring system (made by BAS Inc.) was used for carrying out potential scanning under conditions of a potential range of 400 to 700 mV, a scanning speed of 50 mVsec⁻¹ and 30 potential scanning cycles. The intended compound polymerized on the electrode was obtained.

Black solid

TOF-MS: m/z 415 (monomer), 772 (dimer), 1156 (trimer).

Example 7

Synthesis of poly{2,3-di(4-methylphenyl)-5-(4-aminophenyl)-aminoquinoxaline}

Using a three-electrode beaker cell equipped with a platinum mesh counter electrode, the intended product was synthesized by carrying out electrolytic oxidation according to a potential scanning procedure. More particularly, there was used a solution of 0.21 mg (0.5 mmol) of 2,3-di(4-methylphenyl)-5-(4-aminophenyl)aminoquinoxaline and 1.05 ml (11 mmol) of perchloric acid dissolved in 6.5 g of N,N-dimethylformamide. Electrolytic polymerization was conducted in such a way that a test electrode substrate used was a platinum sheet (1.0 cm² per surface) abraded with an emery paper on the surface thereof, a reference electrode was Ag/Ag⁺, and an electrochemical measuring system (made by BAS Inc.) was used for carrying out potential scanning under conditions of a potential range of 1300 to 1600 mV, a scanning speed of 100 mVsec⁻¹ and 30 potential scanning cycles. The intended polymerized compound polymerized on the electrode was obtained.

Black solid

TOF-MS: m/z 429 (monomer), 826 (dimer), 1240 (trimer), 1667 (tetramer)

Example 8

Synthesis of poly(2,3-di(2-thienyl)-5-(4-aminophenyl)-aminoquinoxaline)

Using a three-electrode beaker cell equipped with a platinum mesh counter electrode, the intended product was synthesized by carrying out electrolytic oxidation according to a potential scanning procedure. More particularly, there was used a solution of 0.20 mg (0.5 mmol) of 2,3-di(2-thienyl)-5-(4-aminophenyl)aminoquinoxaline and 1.05 ml (11 mmol) of perchloric acid dissolved in 6.5 g of N,N-dimethylformamide. Electrolytic polymerization was conducted in such a way that a test electrode substrate used was a platinum sheet (1.0 cm² per surface) abraded with an emery paper on the surface thereof, a reference electrode was Ag/Ag⁺, and an electrochemical measuring system (made by BAS Inc.) was used for carrying out potential scanning under conditions of a potential range of 400 to 700 mV, a scanning speed of 100 mVsec⁻¹ and 30 potential scanning cycles. The intended compound polymerized on the electrode was obtained.

Black solid

TOF-MS: m/z 398 (monomer), 793 (dimer), 1192 (trimer), 1602 (tetramer), 1987 (pentamer)

Example 9

Synthesis of poly{N-4-aminophenyl-10-aminodibenzo(A,C)-phenazine

Using a three-electrode beaker cell equipped with a platinum mesh counter electrode, the intended product was synthesized by carrying out electrolytic oxidation according to a potentiostatics. More particularly, there was used a solution of 0.19 mg (0.5 mmol) of N-4-aminophenyl-10-aminodibenzo(A,C)phenazine and 1.05 ml (11 mmol) of perchloric acid dissolved in 6.5 g of N,N-dimethylformamide. Using a platinum sheet (1.0 cm² per surface) abraded with an emery paper on the surface thereof as a test electrode substrate, Ag/Ag⁺ as reference electrode, and an electrochemical measuring system (made by BAS Inc.), electrolytic polymerization was conducted at a potential set at 800 mV until an electric quantity of 4 coulombs per unit cm² passed. A black film of the intended compound polymerized on the electrode was obtained.

TOF-MS: m/z 781.1 (dimer), 1167.1 (trimer), 1552.5 (tetramer), 1939.5 (pentamer)

Example 10

Synthesis of poly{N-4-aminophenyl-10-aminodibenzo-(A,C)phenazine}

Using a three-electrode beaker cell equipped with a platinum mesh counter electrode, the intended product was synthesized by carrying out electrolytic oxidation according to a potentiostatics. More particularly, there was used a solution of 0.15 mg (0.5 mmol) of 10-aminodibenzo(A,C)phenazine and 1.05 ml (11 mmol) of perchloric acid dissolved in 6.5 g of N,N-dimethylformamide. Electrolytic polymerization was conducted in such a way that a test electrode substrate used was a platinum sheet (1.0 cm² per surface) abraded with an emery paper on the surface thereof, a reference electrode was Ag/Ag⁺, and an electrochemical measuring system (made by BAS Inc.) was used wherein the potential was set at 900 mV and electrolytic polymerization was carried out until an electric quantity of 4 coulombs passed. A black film of the intended compound polymerized on the electrode was obtained.

Black film

TOF-MS: m/z 596.9 (dimer), 893.9 (trimer), 1192.3 (tetramer), 1488.5 (pentamer), 1788.7 (hexamer), 2088.9 (heptamer)

The invention claimed is:

1. An aminoquinoxaline compound of the following formula (1a)

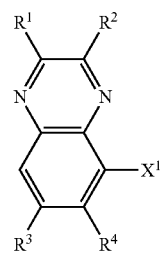

(1a)

wherein R¹ and R² independently represent a hydrogen atom, a hydroxyl group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when R¹ and R² are, respectively, the above-defined phenyl, pyridyl, biphenyl, naphthyl, thienyl, pyrolyl, furyl or condensed heteroaryl group, these groups may be joined through a single bond;

$R^3$ and $R^4$ independently represent a hydrogen atom, a halogen atom, a cyano group, a nitro group, an amino group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^3$ and $R^4$ are, respectively, the above-defined phenyl, pyridyl, biphenyl, naphthyl, thienyl, pyrolyl, furyl or condensed heteroaryl group, these groups may be joined through a single bond;

$X^1$ represents —NH—$R^5$—$NH_2$;

$R^5$ represents a divalent benzene ring which may be substituted with Y;

Y represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z provided that if Y is two or more in number, Y may be the same or different; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group provided that if Z is two or more in number, Z may be the same or different.

2. The aminoquinoxaline compound according to claim 1, wherein $R^1$ and $R^2$ in the above formula (1) independently represent a group of the following formula (2)

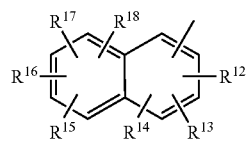

(2)

wherein $R^7$-$R^{11}$ independently represent a hydrogen atom, a halogen atom, a cyano group, a nitro group, an amino group, an epoxy group, a vinyl group, a $C_1$-$C_{10}$ alkyl group, a $C_1$-$C_4$ haloalkyl group, a $C_1$-$C_{10}$ alkoxy group, a $C_1$-$C_4$ cyanoalkyl group, a phenyl group which may be substituted with Z, a naphthyl group which may be substituted with Z or a thienyl group which may be substituted with Z; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group.

3. The aminoquinoxaline compound according to claim 1, wherein $R^1$ and $R^2$ in the above formula (1) independently represent a group of the following formula (3)

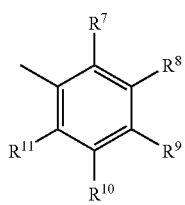

(3)

wherein $R^{12}$-$R^{18}$ independently represent, each substituted at an arbitrary position on the ring of the formula, a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group.

4. The aminoquinoxaline compound according to claim 1, wherein $R^1$ and $R^2$ in the above formula (1) independently represent a group of the following formula (4)

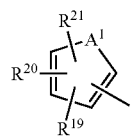

(4)

wherein $R^{19}$-$R^{21}$ independently represent, each substituted at an arbitrary position on the ring of the formula, a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z;

Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group; and $A^1$ represents NH, O or S.

5. The aminoquinoxaline compound according to claim 1, wherein $R^1$ and $R^2$ in the above formula (1) represent a group of the following formula (5)

(5)

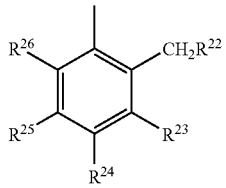

wherein $R^{22}$ represents a halogen atom or a cyano group, $R^{23}$-$R^{26}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group.

6. The aminoquinoxaline compound according to claim 1, wherein $R^5$ in the formula (1) represents a group of the following formula (6)

(6)

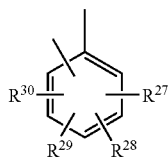

wherein $R^{27}$-$R^{30}$ independently represent, each substituted at an arbitrary position on the ring of the formula, a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group.

7. The aminoquinoxaline compound according to claim 1, wherein $R^5$ in the formula (1) represents a group of the following formula (7)

(7)

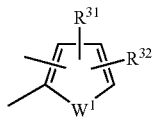

wherein $R^{31}$-$R^{32}$ independently represent, each substituted at an arbitrary position on the ring of the formula, a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z;

Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group; and $W^1$ represents NH, O or S.

8. The aminoquinoxaline compound according to claim 1, wherein $R^5$ in the formula (1) represents a group of the following formula (8)

(8)

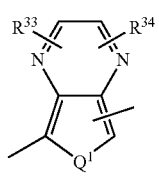

wherein $R^{33}$-$R^{34}$ independently represent, each substituted at an arbitrary position on the ring of the formula, a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z;

Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group; and $Q^1$ represents NH, O or S.

9. The aminoquinoxaline compound according to claim 1, wherein $R^5$ in the formula (1) represents a group of the following formula (9)

(9)

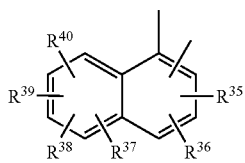

wherein $R^{35}$-$R^{40}$ independently represent, each substituted at an arbitrary position on the ring of the formula, a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group.

10. An aminoquinoxaline compound of the following formula (11)

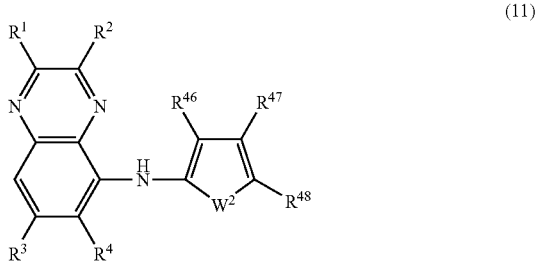

(11)

wherein $R^1$ and $R^2$ independently represent a hydrogen atom, a hydroxyl group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^1$ and $R^2$ are, respectively, the above-defined phenyl, pyridyl, biphenyl, naphthyl, thienyl, pyrolyl, furyl or condensed heteroaryl group, these groups may be joined through a single bond;

$R^3$ and $R^4$ independently represent a hydrogen atom, a halogen atom, a cyano group, a nitro group, an amino group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^3$ and $R^4$ are, respectively, the above-defined phenyl, pyridyl, biphenyl, naphthyl, thienyl, pyrolyl, furyl or condensed heteroaryl group, these groups may be joined through a single bond;

$R^{46}$-$R^{48}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z;

Y represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z provided that if Y is two or more in number, Y may be the same or different;

Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group provided that if Z is two or more in number, Z may be the same or different; and $W^2$ represents NH, O or S.

11. An aminoquinoxaline compound of the following formula (12)

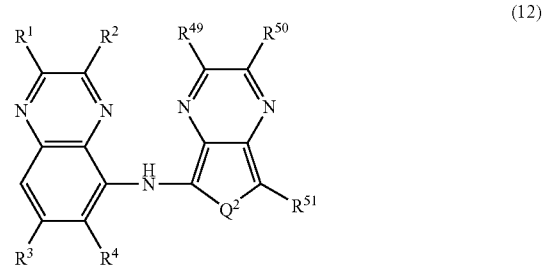

(12)

wherein $R^1$ and $R^2$ independently represent a hydrogen atom, a hydroxyl group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^1$ and $R^2$ are, respectively, the above-defined phenyl, pyridyl, biphenyl, naphthyl, thienyl, pyrolyl, furyl or condensed heteroaryl group, these groups may be joined through a single bond;

$R^3$ and $R^4$ independently represent a hydrogen atom, a halogen atom, a cyano group, a nitro group, an amino group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^3$ and $R^4$ are, respectively, the above-defined phenyl, pyridyl, biphenyl, naphthyl, thienyl, pyrolyl, furyl or condensed heteroaryl group, these groups may be joined through a single bond;

Y represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z provided that if Y is two or more in number, Y may be the same or different;

$R^{49}$-$R^{51}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z;

Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group provided that if Z is two or more in number, Z may be the same or different; and $Q^2$ represents NH, O or S.

12. An aminoquinoxaline compound of the following formula (13)

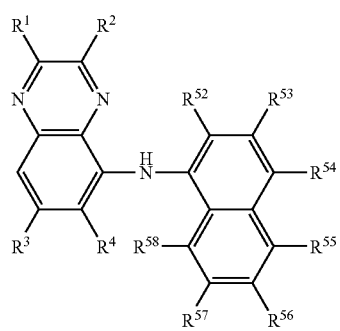

(13)

wherein $R^1$ and $R^2$ independently represent a hydrogen atom, a hydroxyl group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^1$ and $R^2$ are, respectively, the above-defined phenyl, pyridyl, biphenyl, naphthyl, thienyl, pyrolyl, furyl or condensed heteroaryl group, these groups may be joined through a single bond;

$R^3$ and $R^4$ independently represent a hydrogen atom, a halogen atom, a cyano group, a nitro group, an amino group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^3$ and $R^4$ are, respectively, the above-defined phenyl, pyridyl, biphenyl, naphthyl, thienyl, pyrolyl, furyl or condensed heteroaryl group, these groups may be joined through a single bond;

Y represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z provided that if Y is two or more in number, Y may be the same or different;

$R^{52}$-$R^{58}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group provided that if Z is two or more in number, Z may be the same or different.

13. An aminoquinoxaline compound of the following formula (14)

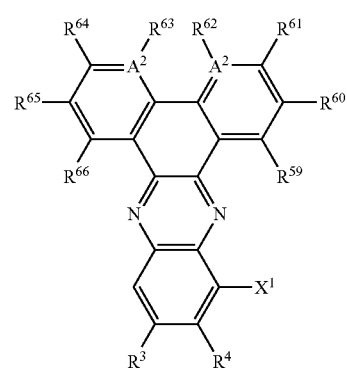

(14)

wherein $R^3$ and $R^4$ independently represent a hydrogen atom, a halogen atom, a cyano group, a nitro group, an amino group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^3$ and $R^4$ are, respectively, the above-defined phenyl, pyridyl, biphenyl, naphthyl, thienyl, pyrolyl, furyl or condensed heteroaryl group, these groups may be joined through a single bond;

$X^1$ represents —NH—$R^5$—$NH_2$ or —NH—$R^6$;

$R^5$ represents a $C_1$-$C_{10}$ alkylene group, a —C(O)$CH_2$—, —$CH_2$C(O)—, a divalent benzene ring which may be substituted with Y, a divalent pyridine ring which may be substituted with Y, a divalent biphenyl group which may be substituted with Y, a divalent naphthalene ring which may be substituted with Y, a divalent thiophene ring which may be substituted with Y, a pyrrole ring which may be substituted with Y, a furan ring which may be substituted with Y, or a condensed hetero ring which may be substituted with Y;

$R^6$ represents a hydrogen atom, a $C_1$-$C_{10}$ alkyl group, an acetyl group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y;

Y represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z provided that if Y is two or more in number, Y may be the same or different;

A2 are each C or N, $R^{59}$-$R^{66}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group provided that if Z is two or more in number, Z may be the same or different, provided that when $A^2$ represents N, $R^{62}$ and $R^{63}$ are both non-existent.

14. An aminoquinoxaline compound of the following formula (1b),

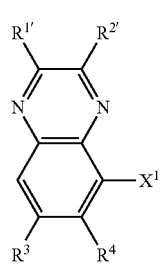

(1b)

wherein $R^{1'}$ and $R^{2'}$ join together to form —CH₂CH₂CH₂—, —CH₂CH₂O—, —OCH₂CH₂—, —CH₂OCH₂—, —OCH₂O—, —CH₂CH₂S—, —SCH₂CH₂—, —CH₂SCH₂—, —CH₂CH₂N(R')—, —N(R')CH₂CH₂—, —CH₂N(R')CH₂—, —CH₂CH₂CH₂CH₂—, —CH₂CH₂CH₂O—, —OCH₂CH₂CH₂—, —CH₂CH₂OCH₂—, —CH₂OCH₂CH₂—, —CH₂OCH₂O—, —OCH₂CH₂O—, —SCH₂CH₂S—, —OCH₂CH₂S—, —SCH₂CH₂O—, —CH₂CH=CH—, —CH=CHCH₂—, —OCH=CH—, —CH=CHO—, —SCH=CH—, —CH=CHS—, —N(R')CH=CH—, —CH=CHN(R')—, —OCH=N—, —N=CHO—, —SCH=N—, —N=CHS—, —N(R')CH=N—, —N=CHN(R')—, —N(R')N=CH—, —CH=N(R')N—, —CH=CHCH=CH—, —OCH₂CH=CH—, —CH=CHCH₂O—, —N=CHCH=CH—, —CH=CHCH=N—, —N=CHCH=N—, —N=CHN=CH—, or —CH=NCH=N— wherein a hydrogen atom bonded to a carbon atom of these groups may be substituted with Y, and R' represents a hydrogen atom, a $C_1$-$C_{10}$ alkyl group, a $C_1$-$C_{10}$ haloalkyl group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z, or a condensed heteroaryl group which may be substituted with Z;

$R^3$ and $R^4$ independently represent a hydrogen atom, a halogen atom, a cyano group, a nitro group, an amino group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^3$ and $R^4$ are, respectively, the above-defined phenyl, pyridyl, biphenyl, naphthyl, thienyl, pyrolyl, furyl or condensed heteroaryl group, these groups may be joined through a single bond;

$X^1$ represents —NH—$R^5$—NH₂ or —NH—$R^6$;

$R^5$ represents a $C_1$-$C_{10}$ alkylene group, —C(O)CH₂—, —CH₂C(O)—, a divalent benzene ring which may be substituted with Y, a divalent pyridine ring which may be substituted with Y, a divalent biphenyl group which may be substituted with Y, a divalent naphthalene ring which may be substituted with Y, a divalent thiophene ring which may be substituted with Y, a pyrrole ring which may be substituted with Y a furan ring which may be substituted with Y, or a condensed hetero ring which may be substituted with Y;

$R^6$ represents a hydrogen atom, a $C_1$-$C_{10}$ alkyl group, an acetyl group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y;

Y represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z provided that if Y is two or more in number, Y may be the same or different; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group, provided that when Z are two or more in number, Z may be the same or different.

15. An aminoquinoxaline compound of the following formula (1c),

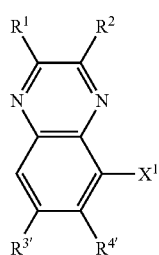

(1c)

wherein $R^1$ and $R^2$ independently represent a hydrogen atom, a hydroxyl group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^1$ and $R^2$ are, respectively, the above-defined phenyl, pyridyl, biphenyl, naphthyl, thienyl, pyrolyl, furyl or condensed heteroaryl group, these groups may be joined through a single bond;

$R^{3'}$ and $R^{4'}$ join together to form —CH$_2$CH$_2$CH$_2$—, —CH$_2$CH$_2$O—, —OCH$_2$CH$_2$—, —CH$_2$OCH$_2$—, —OCH$_2$O—, —CH$_2$CH$_2$S—, —SCH$_2$CH$_2$—, —CH$_2$SCH$_2$—, —CH$_2$CH$_2$N(R')—, —N(R')CH$_2$CH$_2$—, —CH$_2$N(R')CH$_2$—, —CH$_2$CH$_2$CH$_2$CH$_2$—, —CH$_2$CH$_2$CH$_2$O—, —OCH$_2$CH$_2$CH$_2$—, —CH$_2$CH$_2$OCH$_2$—, —CH$_2$OCH$_2$CH$_2$—, —CH$_2$OCH$_2$O—, —OCH$_2$CH$_2$O—, —SCH$_2$CH$_2$S—, —OCH$_2$CH$_2$S—, —SCH$_2$CH$_2$O—, —CH$_2$CH=CH—, —CH=CHCH$_2$—, —OCH=CH—, —CH=CHO—, —SCH=CH—, —CH=CHS—, —N(R')CH=CH—, —CH=CHN(R')—, —OCH=N—, —N=CHO—, —SCH=N—, —N=CHS—, —N(R')CH=N—, —N=CHN(R')—, —N(R')N=CH—, —CH=N(R')N—, —CH=CHCH=CH—, —OCH$_2$CH=CH—, —CH=CHCH$_2$O—, —N=CHCH=CH—, —CH=CHCH=N—, —N=CHCH=N—, —N=CHN=CH—, or —CH=NCH=N—wherein a hydrogen atom bonded to a carbon atom of these groups may be substituted with Y, and R' represents a hydrogen atom, a $C_1$-$C_{10}$ alkyl group, a $C_1$-$C_{10}$ haloalkyl group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z, or a condensed heteroaryl group which may be substituted with Z;

$X^1$ represents —NH—$R^5$—NH$_2$ or —NH—$R^6$;

$R^5$ represents a $C_1$-$C_{10}$ alkylene group, —C(O)CH$_2$—, —CH$_2$C(O)—, a divalent benzene ring which may be substituted with Y, a divalent pyridine ring which may be substituted with Y, a divalent biphenyl group which may be substituted with Y, a divalent naphthalene ring which may be substituted with Y, a divalent thiophene ring which may be substituted with Y, a pyrrole ring which may be substituted with Y, a furan ring which may be substituted with Y, or a condensed hetero ring which may be substituted with Y;

$R^6$ represents a hydrogen atom, a $C_1$-$C_{10}$ alkyl group, an acetyl group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y;

Y represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z provided that if Y is two or more in number, Y may be the same or different; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group, provided that when Z are two or more in number, Z may be the same or different.

16. An aminoquinoxaline compound of the following formula (1d),

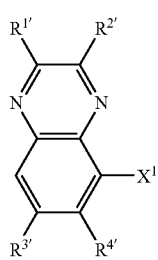

(1d)

wherein $R^{1'}$ and $R^{2'}$ together to form —CH$_2$CH$_2$CH$_2$—, —CH$_2$CH$_2$O—, —OCH$_2$CH$_2$—, —CH$_2$OCH$_2$—, —OCH$_2$O—, —CH$_2$CH$_2$S—, —SCH$_2$CH$_2$—, —CH$_2$SCH$_2$—, —CH$_2$CH$_2$N(R')—, —N(R')CH$_2$CH$_2$—, —CH$_2$N(R')CH$_2$—, —CH$_2$CH$_2$CH$_2$CH$_2$—, —CH$_2$CH$_2$CH$_2$O—, —OCH$_2$CH$_2$CH$_2$—, —CH$_2$CH$_2$OCH$_2$—, —CH$_2$OCH$_2$CH$_2$—, —CH$_2$OCH$_2$O—, —OCH$_2$CH$_2$O—, —SCH$_2$CH$_2$S—, —OCH$_2$CH$_2$S—, —SCH$_2$CH$_2$O—, —CH$_2$CH=CH—, —CH=CHCH$_2$—, —OCH=CH—, —CH=CHO—, —SCH=CH—, —CH=CHS—, —N(R')CH=CH—, —CH=CHN(R')—, —OCH=N—, —N=CHO—, —SCH=N—, —N=CHS—, —N(R')CH=N—, —N=CHN(R')—, —N(R')N=CH—, —CH=N(R')N—, —CH=CHCH=CH—, —OCH$_2$CH=CH—, —CH=CHCH$_2$O—, —N=CHCH=CH—, —CH=CHCH=N—, —N=CHCH=N—, —N=CHN=CH—, or —CH=NCH=N— wherein a hydrogen atom bonded to a carbon atom of these groups may be substituted with Y, and R' represents a hydrogen atom, a $C_1$-$C_{10}$ alkyl group, a $C_1$-$C_{10}$ haloalkyl group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z, or a condensed heteroaryl group which may be substituted with Z, and $R^{3'}$ and $R^{4'}$ join together to form —CH$_2$CH$_2$CH$_2$—, —CH$_2$CH$_2$O—, —OCH$_2$CH$_2$—, —CH$_2$OCH$_2$—, —OCH$_2$O—, —CH$_2$CH$_2$S—, —SCH$_2$CH$_2$—, —CH$_2$SCH$_2$—, —CH$_2$CH$_2$N(R')—, —N(R')CH$_2$CH$_2$—, —CH$_2$N(R')CH$_2$—, —CH$_2$CH$_2$CH$_2$CH$_2$—, —CH$_2$CH$_2$CH$_2$O—, —OCH$_2$CH$_2$CH$_2$—, —CH$_2$CH$_2$OCH$_2$—, —CH$_2$OCH$_2$CH$_2$—, —CH$_2$OCH$_2$O—, —OCH$_2$CH$_2$O—, —SCH$_2$CH$_2$S—, —OCH$_2$CH$_2$S—, —SCH$_2$CH$_2$O—, —CH$_2$CH=CH—, —CH=CHCH$_2$—, —OCH=CH—, —CH=CHO—, —SCH=CH—, —CH=CHS—, —N(R')CH=CH—, —CH=CHN(R')—, —OCH=N—, —N=CHO—, —SCH=N—, —N=CHS—, —N(R')CH=N—, —N=CHN(R')—, —N(R')N=CH—, —CH=N(R')N—, —CH=CHCH=CH—, —OCH$_2$CH=CH—, —CH=CHCH$_2$O—, —N=CHCH=CH—, —CH=CHCH=N—, —N=CHCH=N—, —N=CHN=CH—, or —CH=NCH=N— wherein a hydrogen atom bonded to a carbon atom of these groups may be substituted with Y, and R' represents a hydrogen atom, a $C_1$-$C_{10}$ alkyl group, a $C_1$-$C_{10}$ haloalkyl group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z;

$X^1$ represents —NH—$R^5$—NH$_2$ or —NH—$R^6$;

$R^5$ represents a $C_1$-$C_{10}$ alkylene group, —C(O)CH$_2$—, —CH$_2$C(O)—, a divalent benzene ring which may be substituted with Y, a divalent pyridine ring which may be substituted with Y, a divalent biphenyl group which may be substituted with Y, a divalent naphthalene ring which may be substituted with Y, a divalent thiophene ring which may be substituted with Y, a pyrrole ring which may be substituted with Y, a furan ring which may be substituted with Y, or a condensed hetero ring which may be substituted with Y;

$R^6$ represents a hydrogen atom, a $C_1$-$C_{10}$ alkyl group, an acetyl group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y;

Y represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z provided that if Y is two or more in number, Y may be the same or different; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group, provided that when Z are two or more in number, Z may be the same or different.

17. The aminoquinoxaline compound according to claim 14, wherein the group formed by joining $R^{1'}$ and $R^{2'}$ together is of the following formula (15)

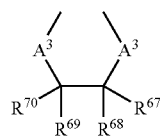

(15)

wherein $A^3$ represents O or S, and $R^{67}$-$R^{70}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group.

18. The aminoquinoxaline compound according to claim 15, wherein the group formed by joining $R^{3'}$ and $R^{4'}$ together is of the following formula (16)

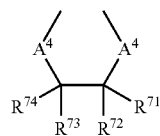

(16)

wherein $A^4$ represents O or S, and $R^{71}$-$R^{74}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group.

19. The aminoquinoxaline compound according to claim 15, wherein the group formed by joining $R^{3'}$ and $R^{4'}$ together is of the following formula (17)

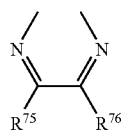

(17)

wherein $R^{75}$ and $R^{76}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group.

20. A polyaminoquinoxaline compound having recurring units of the following formula (18a)

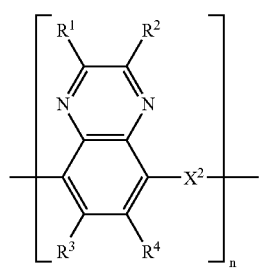

(18a)

wherein $R^1$ and $R^2$ independently represent a hydrogen atom, a hydroxyl group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^1$ and $R^2$ are, respectively, the above-defined phenyl, pyridyl, biphenyl, naphthyl, thienyl, pyrolyl, furyl or condensed heteroaryl group, these groups may be joined through a single bond;

$R^3$ and $R^4$ independently represent a hydrogen atom, a halogen atom, a cyano group, a nitro group, an amino group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^3$ and $R^4$ are, respectively, the above-defined phenyl, pyridyl, biphenyl, naphthyl, thienyl, pyrolyl, furyl or condensed heteroaryl group, these groups may be joined through a single bond;

$X^2$ represents —NH—$R^{77}$—NH— or —NH—$R^{78}$—;

$R^{77}$ and $R^{78}$ independently represent a $C_1$-$C_{10}$ alkylene group, a —C(O)CH$_2$—, —CH$_2$C(O)—, a divalent benzene ring which may be substituted with Y, a divalent pyridine ring which may be substituted with Y, a divalent biphenyl group which may be substituted with Y, a divalent naphthalene ring which may be substituted with Y, a divalent thiophene ring which may be substituted with Y, a divalent pyrrole ring which may be substituted with Y, a divalent furan ring which may be substituted with Y or a condensed hetero ring which may be substituted with Y;

Y represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z provided that if Y is two or more in number, Y may be the same or different;

Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group provided that if Z is two or more in number, Z may be the same or different; and n is an integer of 2 or more.

21. A polyaminoquinoxaline compound having recurring units of the following formula (18b) obtained by polymerizing the monomer defined in claim 14,

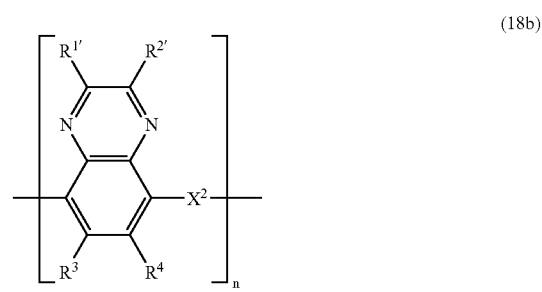

(18b)

wherein $R^{1'}$ and $R^{2'}$ join together to form —CH$_2$CH$_2$CH$_2$—, —CH$_2$CH$_2$O—, —OCH$_2$CH$_2$—, —CH$_2$OCH$_2$—, —OCH$_2$O—, —CH$_2$CH$_2$S—, —SCH$_2$CH$_2$—, —CH$_2$SCH$_2$—, —CH$_2$CH$_2$N(R')—, —N(R')CH$_2$CH$_2$—, —CH₂N(R')CH₂—, —CH₂CH₂CH₂CH₂—, —CH₂CH₂CH₂O—, —OCH₂CH₂CH₂—, —CH₂CH₂OCH₂—, —CH₂OCH₂CH₂—, —CH₂OCH₂O—, —OCH₂CH₂O—, —SCH₂CH₂S—, —OCH₂CH₂S—, —SCH₂CH₂O—, —CH₂CH═CH—, —CH═CHCH₂—, —OCH═CH—, —CH═CHO—, —SCH═CH—, —CH═CHS—, —N(R')CH═CH—, —CH═CHN(R')—, —OCH═N—, —N═CHO—, —SCH═N—, —N═CHS—, —N(R')CH═N—, —N═CHN(R')—, —N(R')N═CH—, —CH═N(R')N—, —CH═CHCH═CH—, —OCH₂CH═CH—, —CH═CHCH₂O—, —N═CHCH═CH—, —CH═CHCH═N—, —N═CHCH═N—, —N═CHN═CH—, or —CH═NCH═N— wherein a hydrogen atom bonded to a carbon atom of these groups may be substituted with Y, and R' represents a hydrogen atom, a C₁-C₁₀ alkyl group, a C₁-C₁₀ haloalkyl group, a C₁-C₁₀ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z;

R³ and R⁴ independently represent a hydrogen atom, a halogen atom, a cyano group, a nitro group, an amino group, a C₁-C₁₀ alkyl group, a C₁-C₁₀ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when R³ and R⁴ are, respectively, the above-defined phenyl, pyridyl, biphenyl, naphthyl, thienyl, pyrolyl, furyl or condensed heteroaryl group, these groups may be joined through a single bond;

X² represents —NH—R⁷⁷—NH— or —NH—R⁷⁸—;

R⁷⁷ and R⁷⁸ independently represent a C₁-C₁₀ alkylene group, —C(O)CH₂—, —CH₂C(O)—, a divalent benzene ring which may be substituted with Y, a divalent pyridine ring which may be substituted with Y, a divalent biphenyl group which may be substituted with Y, a divalent naphthalene ring which may be substituted with Y, a divalent thiophene ring which may be substituted with Y, a divalent pyrrole ring which may be substituted with Y, a divalent furan ring which may be substituted with Y, or a condensed hetero ring which may be substituted with Y;

Y represents a halogen atom, a cyano group, a nitro group, an amino group, an epoxy group, a vinyl group, a C₁-C₁₀ alkyl group, a C₁-C₁₀ haloalkyl group, a C₁-C₁₀ alkoxy group, a C₁-C₁₀ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z provided that if Y is two or more in number, Y may be the same or different;

Z represents a halogen atom, a cyano group, a nitro group, an amino group, an epoxy group, a vinyl group, a C₁-C₁₀ alkyl group, a C₁-C₁₀ haloalkyl group, a C₁-C₁₀ alkoxy group, a C₁-C₁₀ cyanoalkyl group, a phenyl group, a biphenyl group, a naphthyl group, a thienyl group, a pyrolyl group, a furyl group or a condensed heteroaryl group, provided that when Z are two or more in number, Z may be the same or different; and n is an integer of 2 or more.

22. A polyaminoquinoxaline compound having recurring units of the following formula (18c) obtained by polymerizing the monomer defined in claim 15,

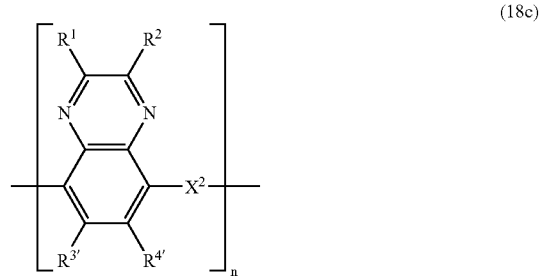

(18c)

wherein R¹ and R² independently represent a hydrogen atom, a hydroxyl group, a C₁-C₁₀ alkyl group, a C₁-C₁₀ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when R¹ and R² are, respectively, the above-defined phenyl, pyridyl, biphenyl, naphthyl, thienyl, pyrolyl, furyl or condensed heteroaryl group, these groups may be joined through a single bond;

R³' and R⁴' join together to form —CH₂CH₂CH₂—, —CH₂CH₂O—, —OCH₂CH₂—, —CH₂OCH₂—, —OCH₂O—, —CH₂CH₂S—, —SCH₂CH₂—, —CH₂SCH₂—, —CH₂CH₂N(R')—, —N(R')CH₂CH₂—, —CH₂N(R')CH₂—, —CH₂CH₂CH₂CH₂—, —CH₂CH₂CH₂O—, —OCH₂CH₂CH₂—, —CH₂CH₂OCH₂—, —CH₂OCH₂CH₂—, —CH₂OCH₂O—, —OCH₂CH₂O—, —SCH₂CH₂S—, —OCH₂CH₂S—, —SCH₂CH₂O—, —CH₂CH═CH—, —CH═CHCH₂—, —OCH═CH—, —CH═CHO—, —SCH═CH—, —CH═CHS—, —N(R')CH═CH—, —CH═CHN(R')—, —OCH═N—, —N═CHO—, —SCH═N—, —N═CHS—, —N(R')CH═N—, —N═CHN(R')—, —N(R')N═CH—, —CH═N(R')N—, —CH═CHCH═CH—, —OCH₂CH═CH—, —CH═CHCH₂O—, —N═CHCH═CH—, —CH═CHCH═N—, —N═CHCH═N—, —N═CHN═CH—, or —CH═NCH═N— wherein a hydrogen atom bonded to a carbon atom of these groups may be substituted with Y, and R' represents a hydrogen atom, a C₁-C₁₀ alkyl group, a C₁-C₁₀ haloalkyl group, a C₁-C₁₀ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z, or a condensed heteroaryl group which may be substituted with Z;

$X^2$ represents —NH—$R^{77}$—NH— or —NH—$R^{78}$—;

$R^{77}$ and $R^{78}$ independently represent a $C_1$-$C_{10}$ alkylene group, —C(O)CH$_2$—, —CH$_2$C(O)—, a divalent benzene ring which may be substituted with Y, a divalent pyridine ring which may be substituted with Y, a divalent biphenyl group which may be substituted with Y, a divalent naphthalene ring which may be substituted with Y, a divalent thiophene ring which may be substituted with Y, a divalent pyrrole ring which may be substituted with Y, a divalent furan ring which may be substituted with Y, or a condensed hetero ring which may be substituted with Y;

Y represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z provided that if Y is two or more in number, Y may be the same or different;

Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group, provided that when Z are two or more in number, Z may be the same or different; and n is an integer of 2 or more.

23. A polyaminoquinoxaline compound having recurring units of the following formula (18d) obtained by polymerizing the monomer defined in claim 16,

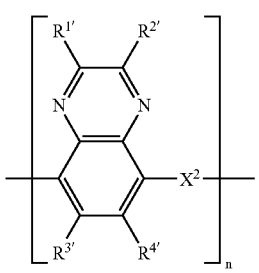

(18d)

wherein $R^{1'}$ and $R^{2'}$ join together to form —CH$_2$CH$_2$CH$_2$—, —CH$_2$CH$_2$O—, —OCH$_2$CH$_2$—, —CH$_2$OCH$_2$—, —OCH$_2$O—, —CH$_2$CH$_2$S—, —SCH$_2$CH$_2$—, —CH$_2$SCH$_2$—, —CH$_2$CH$_2$N(R')—, —N(R')CH$_2$CH$_2$—, —CH$_2$N(R')CH$_2$—, —CH$_2$CH$_2$CH$_2$CH$_2$—, —CH$_2$CH$_2$CH$_2$O—, —OCH$_2$CH$_2$CH$_2$—, —CH$_2$CH$_2$OCH$_2$—, —CH$_2$OCH$_2$CH$_2$—, —CH$_2$OCH$_2$O—, —OCH$_2$CH$_2$O—, —SCH$_2$CH$_2$S—, —OCH$_2$CH$_2$S—, —SCH$_2$CH$_2$O—, —CH$_2$CH=CH—, —CH=CHCH$_2$—, —OCH=CH—, —CH=CHO—, —SCH=CH—, —CH=CHS—, —N(R')CH=CH—, —CH=CHN(R')—, —OCH=N—, —N=CHO—, —SCH=N—, —N=CHS—, —N(R')CH=N—, —N=CHN(R')—, —N(R')N=CH—, —CH=N(R')N—, —CH=CHCH=CH—, —OCH$_2$CH=CH—, —CH=CHCH$_2$O—, —N=CHCH=CH—, —CH=CHCH=N—, —CH=CHCH=N—, —N=CHCH=N—, —N=CHN=CH—, or —CH=NCH=N— wherein a hydrogen atom bonded to a carbon atom of these groups may be substituted with Y, and R' represents a hydrogen atom, a $C_1$-$C_{10}$ alkyl group, a $C_1$-$C_{10}$ haloalkyl group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z, and $R^{3'}$ and $R^{4'}$ join together to form —CH$_2$CH$_2$CH$_2$—, —CH$_2$CH$_2$O—, —OCH$_2$CH$_2$—, —CH$_2$OCH$_2$—, —OCH$_2$O—, —CH$_2$CH$_2$S—, —SCH$_2$CH$_2$—, —CH$_2$SCH$_2$—, —CH$_2$CH$_2$N(R')—, —N(R')CH$_2$CH$_2$—, —CH$_2$N(R)CH$_2$—, —CH$_2$CH$_2$CH$_2$CH$_2$—, —CH$_2$CH$_2$CH$_2$O—, —OCH$_2$CH$_2$CH$_2$—, —CH$_2$CH$_2$OCH$_2$—, —CH$_2$OCH$_2$CH$_2$—, —CH$_2$OCH$_2$O—, —OCH$_2$CH$_2$O—, —SCH$_2$CH$_2$S—, —OCH$_2$CH$_2$S—, —SCH$_2$CH$_2$O—, —CH$_2$CH=CH—, —CH=CHCH$_2$—, —OCH=CH—, —CH=CHO—, —SCH=CH—, —CH=CHS—, —N(R')CH=CH—, —CH=CHN(R')—, —OCH=N—, —N=CHO—, —SCH=N—, —N=CHS—, —N(R')CH=N—, —N=CHN(R')—, —N(R')N=CH—, —CH=N(R')N—, —CH=CHCH=CH—, —OCH$_2$CH=CH—, —CH=CHCH$_2$O—, —N=CHCH=CH—, —CH=CHCH=N—, —N=CHCH=N—, —N=CHN=CH—, or —CH=NCH=N— wherein a hydrogen atom bonded to a carbon atom of these groups may be substituted with Y, and R' represents a hydrogen atom, a $C_1$-$C_{10}$ alkyl group, a $C_1$-$C_{10}$ haloalkyl group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z;

$X^2$ represents —NH—$R^{77}$—NH— or —NH—$R^{78}$—;

$R^{77}$ and $R^{78}$ independently represent a $C_1$-$C_{10}$ alkylene group, —C(O)CH$_2$—, —CH$_2$C(O)—, a divalent benzene ring which may be substituted with Y, a divalent pyridine ring which may be substituted with Y, a divalent biphenyl group which may be substituted with Y, a divalent naphthalene ring which may be substituted with Y, a divalent thiophene ring which may be substituted with Y, a divalent pyrrole ring which may be substituted with Y, a divalent furan ring which may be substituted with Y or a condensed hetero ring which may be substituted with Y;

Y represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z provided that if Y is two or more in number, Y may be the same or different; and Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group, provided that when Z are two or more in number, Z may be the same or different; and n is an integer of 2 or more.

24. A film obtained by use of any one of an aminoquinoxaline compound as defined in claim 1 or a polyaminoquinoxaline compound as defined in claim 20.

25. The film according to claim 24, wherein the film is prepared by spin coating, casting or vacuum deposition.

26. The film according to claim 24, wherein the film is obtained by compression molding.

27. An electro chromic device made by use of any one of an aminoquinoxaline compound as defined in claim 1 or a polyaminoquinoxaline compound as defined in claim 20.

28. A semiconductor device made by use of any one of an aminoquinoxaline compound as defined in claim 1 or a polyaminoquinoxaline compound as defined in claim 20.

29. A p-type semiconductor obtained by oxidizing, with an oxidizing agent or through electrochemical doping, any one of an aminoquinoxaline compound as defined in claim 1 or a polyaminoquinoxaline compound as defined in claim 20.

30. An n-type semiconductor obtained by reducing, with a reducing agent or through electrochemical doping, any one of an aminoquinoxaline compound as defined in claim 1 or a polyaminoquinoxaline compound as defined in claim 20.

31. A solar cell made by use of a p-type semiconductor and an n-type semiconductor,
   wherein the p-type semiconductor is obtained by oxidizing, with an oxidizing agent or through electrochemical doping, any one of an aminoquinoxaline compound as defined in claim 1 or a polyaminoquinoxaline compound as defined in claim 20, and
   wherein the n-type semiconductor is obtained by reducing, with a reducing agent or through electrochemical doping, any one of an aminoquinoxaline compound as defined in claim 1 or a polyaminoquinoxaline compound as defined in claim 20.

32. An organic electroluminescent device made by use of any one of an aminoquinoxaline compound as defined in claim 1 or a polyaminoquinoxaline compound as defined in claim 20.

33. A non-linear organic material made by use of any one of an aminoquinoxaline compound as defined in claim 1 or a polyaminoquinoxaline compound as defined in claim 21.

34. A polyaminoquinoxaline compound having recurring units of the following formula (18a') obtained by polymerizing the monomer of claim 13,

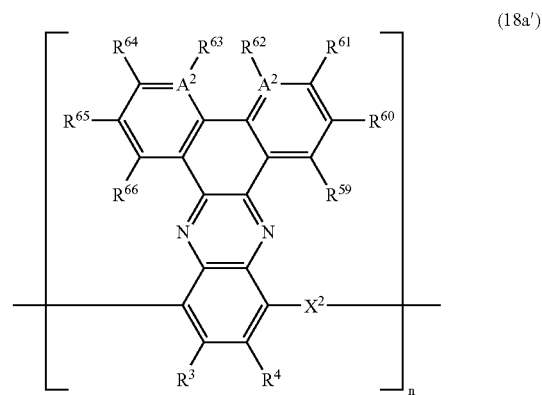

wherein $R^3$ and $R^4$ independently represent a hydrogen atom, a halogen atom, a cyano group, a nitro group, an amino group, a $C_1$-$C_{10}$ alkyl group, a $C_1$-$C_{10}$ alkoxy group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y provided that when $R^3$ and $R^4$ are, respectively, the above-defined phenyl, pyridyl, biphenyl, naphthyl, thienyl, pyrolyl, furyl or condensed heteroaryl group, these groups may be joined through a single bond;

$X^2$ represents —NH—$R^5$—$NH_2$ or —NH—$R^6$;

$R^5$ represents a $C_1$-$C_{10}$ alkylene group, a —C(O)$CH_2$—, —$CH_2$C(O)—, a divalent benzene ring which may be substituted with Y, a divalent pyridine ring which may be substituted with Y, a divalent biphenyl group which may be substituted with Y, a divalent naphthalene ring which may be substituted with Y, a divalent thiophene ring which may be substituted with Y, a pyrrole ring which may be substituted with Y, a furan ring which may be substituted with Y, or a condensed hetero ring which may be substituted with Y;

$R^6$ represents a hydrogen atom, a $C_1$-$C_{10}$ alkyl group, an acetyl group, a phenyl group which may be substituted with Y, a pyridyl group which may be substituted with Y, a biphenyl group which may be substituted with Y, a naphthyl group which may be substituted with Y, a thienyl group which may be substituted with Y, a pyrolyl group which may be substituted with Y, a furyl group which may be substituted with Y or a condensed heteroaryl group which may be substituted with Y;

Y represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group which may be substituted with Z, a pyridyl group which may be substituted with Z, a biphenyl group which may be substituted with Z, a naphthyl group which may be substituted with Z, a thienyl group which may be substituted with Z, a pyrolyl group which may be substituted with Z, a furyl group which may be substituted with Z or a condensed heteroaryl group which may be substituted with Z provided that if Y is two or more in number, Y may be the same or different;

A2 are each C or N, $R^{59}$-$R^{66}$ independently represent a hydrogen atom, a halogen atom, a cyano group, a nitro group, an amino group, an epoxy group, a vinyl group, a $C_1$-$C_{10}$ alkyl group, a $C_1$-$C_{10}$ alkoxy group, a phenyl group which may be substituted with Z, a naphthyl group which may be substituted with Z or a thienyl group which may be substituted with Z, provided that when $A^2$ represents N, $R^{62}$ and $R^{63}$ are both non-existent;

Z represents a halogen atom, a cyano group, a nitro group, an amino group, an epoxy group, a vinyl group, a $C_1$-$C_{10}$ alkyl group, a $C_1$-$C_{10}$ haloalkyl group, a $C_1$-$C_{10}$ alkoxy group, a $C_1$-$C_{10}$ cyanoalkyl group, a phenyl group, a biphenyl group, a naphthyl group, a thienyl group, a pyrolyl group, a furyl group or a condensed heteroaryl group, provided that if Z is two or more in number, Z may be the same or different; and n is an integer of 2 or more.

* * * * *